United States Patent
Ramamurthy

(10) Patent No.: US 11,627,936 B2
(45) Date of Patent: Apr. 18, 2023

(54) SYSTEMS AND METHODS FOR ULTRASOUND REVIEW AND IMAGING

(71) Applicant: Cordance Medical Inc., Los Altos, CA (US)

(72) Inventor: Bhaskar Ramamurthy, Los Altos, CA (US)

(73) Assignee: Cordance Medical Inc., Los Altos, CA (US)

( * ) Notice: Subject to any disclaimer, the term of this patent is extended or adjusted under 35 U.S.C. 154(b) by 342 days.

(21) Appl. No.: 16/324,542

(22) PCT Filed: Aug. 16, 2017

(86) PCT No.: PCT/US2017/047203
§ 371 (c)(1),
(2) Date: Feb. 8, 2019

(87) PCT Pub. No.: WO2018/035256
PCT Pub. Date: Feb. 22, 2018

(65) Prior Publication Data
US 2019/0183457 A1    Jun. 20, 2019

Related U.S. Application Data

(60) Provisional application No. 62/375,476, filed on Aug. 16, 2016, provisional application No. 62/473,422, filed on Mar. 19, 2017.

(51) Int. Cl.
*A61B 8/14*    (2006.01)
*G01S 7/52*    (2006.01)
(Continued)

(52) U.S. Cl.
CPC ............... *A61B 8/14* (2013.01); *A61B 8/00* (2013.01); *G01S 7/003* (2013.01);
(Continued)

(58) Field of Classification Search
None
See application file for complete search history.

(56) References Cited

U.S. PATENT DOCUMENTS 5,072,735 A    12/1991  Okazaki et al.
6,716,172 B1 *  4/2004  Kerby .................... A61B 8/463
                                                         600/443
(Continued)

FOREIGN PATENT DOCUMENTS

CN    101999905 A    4/2011
CN    104939869 A    9/2015
(Continued)

OTHER PUBLICATIONS

Notice of Reasons for Refusal, dated Jun. 15, 2021, issued for Japanese Patent Application No. 2019-508813, 12 pages (with English translation).
(Continued)

*Primary Examiner* — Amelie R Davis
*Assistant Examiner* — Marjan Saboktakin
(74) *Attorney, Agent, or Firm* — Klarquist Sparkman, LLP

(57) ABSTRACT

A system for reviewing results of ultrasound examinations provides enhanced control over reviewed images. A review and imaging system receives additional data comprising one or more of additional ultrasound images generated using parameter settings different from those selected by and sonographer and earlier stage ultrasound data. An ultrasound machine may be configured to acquire and make the additional data available to the review and imaging system. The review and imaging system may provide a wide range of control options for obtaining optimized display of images based on the additional data.

19 Claims, 24 Drawing Sheets

(51) Int. Cl.
  *G01S 7/00* (2006.01)
  *A61B 8/00* (2006.01)
  *A61B 8/08* (2006.01)
  *G16H 30/40* (2018.01)

(52) U.S. Cl.
  CPC ......... *G01S 7/52098* (2013.01); *G16H 30/40* (2018.01); *A61B 8/5207* (2013.01)

(56) References Cited

U.S. PATENT DOCUMENTS

| | | |
|---|---|---|
| 7,062,714 B1 | 6/2006 | Mo et al. |
| 8,491,479 B2 | 7/2013 | Pelissier et al. |
| 8,545,405 B2 | 10/2013 | Raghavan et al. |
| 2007/0161898 A1 | 7/2007 | Hao et al. |
| 2012/0004545 A1 | 1/2012 | Ziv-Ari et al. |
| 2015/0153990 A1 | 6/2015 | Rust et al. |

FOREIGN PATENT DOCUMENTS

| | | |
|---|---|---|
| CN | 105496459 A | 4/2016 |
| JP | 2008-136867 A | 6/2008 |
| JP | 2016-022297 A | 2/2016 |
| WO | WO 2016/028787 A1 | 2/2016 |

OTHER PUBLICATIONS

Extended European Search Report for European Application No. 17842075.8, dated Mar. 13, 2020.

International Search Report and Written Opinion for PCT/US2017/047203, dated Dec. 26, 2017.

Office Action, dated Mar. 10, 2022, issued for Chinese Patent Application No. 201780055957.8, 27 pages with English translation.

\* cited by examiner

|  | Frequency (MHz) | Depth (mm) | Transmit focus (mm) |
|---|---|---|---|
| Time period 1: 5s | 2 | 70 | 50 |
| Time period 2: 5s | 2 | 100 | 50 |
| Time period 3: 5s | 2 | 150 | 50 |

FIG. 17A

|  | Frequency (MHz) | Depth (mm) | Transmit focus (mm) |
|---|---|---|---|
| Time period 1: 5s | 7 | 40 | 20 |
| Time period 2: 5s | 10 | 40 | 20 |

FIG. 17B

|  | Frequency (MHz) | Depth (mm) | Transmit focus (mm) | Type of data to capture & store |
|---|---|---|---|---|
| Time period 1: 5s | 2 | 70 | 50 | Channel by channel RF, scan converted |
| Time period 2: 5s | 2 | 100 | 50 | Channel by channel RF, scan converted |
| Time period 3: 5s | 2 | 150 | 50 | Channel by channel RF, scan converted |

FIG. 17C

|  | Frequency (MHz) | Depth (mm) | Transmit focus (mm) | Elevation Scan angle (deg) | Azimuthal scan angle (deg) | Type of data to capture & store |
|---|---|---|---|---|---|---|
| Time period 1: 5s | 7 | 40 | 20 | 5 | 10 | Line by line pre-scan converted data |
| Time period 2: 5s | 10 | 30 | 20 | 10 | 10 | Line by line pre-scan converted data |

FIG.19

| | Frequency (MHz) | Depth (mm) | Transmit focus (mm) | Elevation Scan angle (deg) | Azimuthal scan angle (deg) | Type of data to capture & store | Rule for amount of data to be captured |
|---|---|---|---|---|---|---|---|
| Time period 1: 5s | 7 | 40 | 20 | 5 | 10 | Channel by channel RF, scan converted | RF: 1 Every 0.5 s |
| Time period 2: 5s | 10 | 30 | 20 | 5 | 10 | Channel by channel RF, scan converted | RF: 1 Every 0.5 s |

FIG. 21

SYSTEMS AND METHODS FOR ULTRASOUND REVIEW AND IMAGING

CROSS-REFERENCE TO RELATED APPLICATIONS

This application is the U.S. National Stage of International Application No. PCT/US2017/047203, filed Aug. 16, 2017, which was published in English under PCT Article 21(2), which in turn claims the benefit of U.S. Provisional Application No. 62/473,422, filed Mar. 19, 2017, and from U.S. Provisional Application No. 62/375,476, filed Aug. 16, 2016. For the purposes of the United States, this application claims the benefit under 35 U.S.C. § 119 of U.S.Provisional Application No. 62/473,422, filed Mar. 19, 2017, entitled ULTRASOUND REVIEW AND IMAGING SYSTEMS AND RELATED METHODS, and U.S.Provisional Application No. 62/375,476, filed Aug. 16, 2016, entitled AN ADVANCED ULTRASOUND REVIEW AND IMAGING SYSTEM, which are hereby incorporated herein by reference for all purposes.

FIELD

This invention relates to ultrasound imaging, methods and apparatus for medical ultrasound imaging, and methods and apparatus for facilitating review of previously-acquired ultrasound data.

BACKGROUND

In a typical workflow in a laboratory that acquires ultrasound images, a physician requests a certain type of ultrasound examination of a patient; a sonographer (or "ultrasound technician") performs the requested ultrasound examination of the patient using an ultrasound machine; the ultrasound machine acquires certain images of the patient; the acquired images are stored in the ultrasound machine; the stored images are transferred to an institution-wide network such as a hospital network; and a physician and/or specialist reviews the ultrasound images using a computer connected to the institution-wide network.

The images that are stored in ultrasound machines, and subsequently transferred to institution-wide networks, are typically output by final stages of a multi-stage image processing chain within the ultrasound machine. For example, most ultrasound machines store scan-converted images but not line-by-line radio frequency (RF) data.

All too often, the images resulting from an ultrasound examination are inadequate or non-diagnostic. Examples of inadequacies include, but are not limited to: inadequate gain, inappropriate frequency, inappropriate depth, inappropriate field-of-view and inadequate zoom. These inadequacies may force a physician reviewing the ultrasound images to order another ultrasound examination for the same patient.

Currently available picture archiving and communication systems (PACS) provide basic image review capabilities such as measurements and annotation. Advanced PACS systems may provide controls through which basic parameters such as gain can be adjusted. However, most ultrasound review stations provide few options for adjusting ultrasound images to help physicians accurately analyze ultrasound images and efficiently diagnose conditions of the patient based on the ultrasound images.

For example, existing review stations may provide the ability to change the overall gain of an ultrasound image, but not gain on a line-by-line basis.

There is a need for methods and systems that facilitate comprehensive review of ultrasound data after a live imaging session. There is also a need for methods and systems that can efficiently acquire more comprehensive ultrasound data.

SUMMARY

This invention has a number of aspects that may be applied together, individually and in any sub-combinations. These include, without limitation:
  systems including review and imaging systems configured to permit reviewers of previously-acquired images, to conveniently change imaging settings and optimize the images.
  systems including review and imaging systems configured to permit reviewers of previously-acquired echo data, to conveniently create new images and/or adjust images derived from the echo data.
  ultrasound machines adapted to acquire and store additional data that may be applied for after-the-fact creation of new images, optimization of such images and/or adjustment of ultrasound images.
  ultrasound review and imaging systems that are configurable to emulate controls of different ultrasound machines.
  ultrasound review and imaging systems including tools that assist in the analysis of ultrasound data and ultrasound images.
  ultrasound review and imaging systems configured to allow reviewers to modify system parameters on the review and imaging system.
  medical information systems including ultrasound review stations and/or ultrasound machines as described herein.

One example aspect provides an ultrasound review and imaging system capable of generating new images and/or altering previously-generated ultrasound images. The review and imaging system may optionally include an analysis engine operative to derive and present additional information about the image to a reviewer.

Another example aspect provides a method of modifying images generated by an ultrasound machine and/or forming new images entirely, based on ultrasound data previously acquired, captured and stored on the ultrasound machine. The method provides information on which a new diagnosis may be based, as opposed to the case where a diagnosis is based only on images as generated at the ultrasound machine. The method provides benefits that may be realized after the live imaging session has concluded, and may avoid the need to call a patient back for a repeat examination.

Some aspects of the invention involve the transfer of data of data types that are not usually provided outside of an ultrasound machine, from an ultrasound machine to an archival system or a review and imaging system. In some embodiments, such data is transmitted using a "private" mode provided by the Digital Imaging and Communications in Medicine (DICOM) standard. Private mode permits any information that does not confirm to the DICOM standard to be communicated between systems and/or machines that are enabled to transmit and receive "private" data. Private data or information may be any data or information that is not part of the published DICOM standard (e.g. ultrasound machine settings, computation algorithms, radio-frequency echo data, ultrasound data that are not scan-converted data, etc.).

An example aspect of the invention provides an ultrasound imaging system comprising at least one ultrasound imaging machine and at least one review and imaging system in data communication with the ultrasound imaging machine. The review and imaging system is operable to process data originating from the ultrasound imaging machine and to display a resulting image on a display of the review and imaging system. The ultrasound imaging machine comprises an ultrasound transmitter, an ultrasound receiver connected to receive ultrasound echo signals from an ultrasound transducer, an image processing chain configured to process the echo signals to yield image data, a display operative to display the image data and a user interface operative to receive user settings for one or more parameters that affect quality of the image data. The ultrasound machine is configured to make the image data and additional data available to the review and imaging system. The additional data including one or more of: data obtained using settings different from the user settings; and data from a stage of the image processing chain upstream from the image data. For example, the additional data may comprise one or more of channel-by-channel RF data, summed line-by-line RF data, detected line-by-line data, pre-scan converted image data and post scan converted data.

The review and imaging station may comprise a user interface that provides controls operable to adjust settings that affect quality of the resulting image. The review and imaging station may be configured to process the additional data to determine available settings and to display the available settings. The user interface of the review and imaging station may be used to select settings from among the available settings. The available settings may vary depending on the type(s) of data included in the additional data.

The user interface of the review and imaging station may comprise controls operable to select one or more of:
an imaging depth different from an imaging depth specified in the user settings;
a transmit focus different from a transmit focus specified in the user settings;
a gain;
a transmit frequency; and
an apodization function.
The controls may be operable to adjust gain on a line-by-line basis.

In some embodiments the ultrasound machine is configured to: automatically alter a transmit frequency; operate the transmitter to transmit ultrasound energy at the altered transmit frequency and operate the receiver to receive corresponding echo signals; and include in the additional data the corresponding echo signals or data obtained by processing the corresponding echo signals.

In some embodiments the ultrasound machine is configured to: automatically alter the user settings to obtain altered settings; transmit ultrasound energy and receive corresponding echo signals; and process the echo signals wherein at least one of transmitting the ultrasound energy, receiving the ultrasound energy and processing the echo signals is based on the altered settings. For example, The ultrasound machine may be configured to, in sequence, obtain a plurality of sets of the additional data, each of the sets obtained using different altered settings.

In some embodiments the review and imaging system provides a multi-stage image processing chain and the additional data includes data of at least one of plural types of data. The plural types of data may be present at corresponding stages of the image processing chain of the ultrasound machine. The review and imaging system may be configured to input the additional data into a stage of the multi-stage image processing chain based on the type of the data.

In some embodiments the review and imaging system provides one or more features for emulating an ultrasound machine, for example the additional data may comprise data specifying a control layout for the ultrasound machine and the review and imaging system may be configured to assign functions to the controls of the user interface of the review and imaging system based on the control layout for the ultrasound machine. As another example the additional data may comprise data specifying one or more image processing algorithms included in the image processing chain of the ultrasound machine and the review and imaging system may be configured to apply the one or more image processing algorithms in processing the additional data.

Data may be encoded in various ways. In some embodiments the ultrasound machine comprises a data encoder configured to encode the image data in DICOM format. The data encoder may be configured to encode the additional data as DICOM private data.

The system may comprise an archival system comprising a data store. The review and imaging system may be configured to retrieve the additional data from the archival system. The review and imaging system may be configured to transmit the resulting image to the archival system and the archival system is configured to store the resulting image in the data store.

Another example aspect of the invention provides a review and imaging system for ultrasound data. The review and imaging system comprises a data communication network interface; a display; a data store; and a controller. The user interface is configured to store ultrasound data received by way of the network interface. The ultrasound data includes image data obtained by an ultrasound machine using user settings and additional data, the additional data including one or more of: data obtained using settings different from the user settings; and data from a stage of an image processing chain of the ultrasound machine upstream from the image data. The user interface is operable to receive input from a reviewer of one or more review settings different from the user settings. The controller is operable to, based on the review settings, select from and/or process the additional data to yield a review image and display the review image on the display. The review and imaging system may have any additional feature(s) described above or elsewhere herein.

In some embodiments the user interface comprises an ultrasound keyboard.

The review and imaging system may comprise an image analyzer operable to perform one or more of:
obtain statistics for the review image;
classify the review image or an region within the review image;
fuse the review image with another image;
perform measurements and/or calculations based on the review image.

In some embodiments the review and imaging system includes a multi-stage image processing chain comprising a plurality of stages connected in series. In such embodiments the controller may be configured to determine a type of a data block included in the additional data, identify one of the stages corresponding to the type of the data block and direct the data block to the identified one of the stages for processing to yield the review image.

The review and imaging system may include a sum—delay-beamformer operable to perform beamforming on RF data included in the additional data.

Another aspect of the invention provides a review and imaging system for ultrasound data. The review and imaging system comprises: a data communication network interface; a data store configured to store ultrasound data originating from an ultrasound machine and received by way of the network interface the ultrasound data including data of two or more of the following types: RF data; pre-scan converted detected data; pre-scan converted image data and scan-converted data. a display; a user interface operable to receive input from a reviewer of one or more review settings and input selecting one of the types of data for processing; and a controller operable to, based on the review settings, apply processing to the ultrasound data to yield a review image and display the review image on the display wherein the processing is based on the selected data type and the review settings. The review and imaging system may have any additional feature(s) described above or elsewhere herein.

Another example aspect of the invention provides an ultrasound machine comprising: an ultrasound transmitter, an ultrasound receiver connected to receive ultrasound echo signals from an ultrasound transducer, an image processing chain configured to process the echo signals to yield image data, a display operative to display the image data; a user interface operative to receive user settings for one or more parameters that affect quality of the image data, the ultrasound machine configured to export the image data and additional data for review by a reviewer the additional data including one or more of: data obtained using settings different from the user settings; and data from a stage of the image processing chain upstream from the image data. The additional data may comprise, for example, one or more of channel-by-channel RF data, summed line-by-line RF data, detected line-by-line data and pre-scan converted image data. The ultrasound machine may be configured to: automatically alter a transmit frequency; operate the transmitter to transmit ultrasound energy at the altered transmit frequency and operate the receiver to receive corresponding echo signals; and include in the additional data the corresponding echo signals or data obtained by processing the corresponding echo signals.

The ultrasound machine may be configured to: automatically alter the user settings to obtain altered settings; transmit ultrasound energy and receive corresponding echo signals; and process the echo signals wherein at least one of transmitting the ultrasound energy, receiving the ultrasound energy and processing the echo signals is based on the altered settings. The altered settings may for example bracket the user settings.

The ultrasound machine may be configured to, in sequence, obtain a plurality of sets of the additional data, each of the sets obtained using different altered settings.

Another example aspect of the invention provides an ultrasound machine comprising: a transducer; a transmit circuit operable to drive the transducer to transmit ultrasound energy; a receive circuit connected to receive echo signals from the transducer; and a controller configured to process the echo signals to yield an ultrasound image and to store the ultrasound image in a data store upon activation of a capture control. The controller is further configured to, upon activation of the capture control, automatically store in the data store at least one of the echo signals and an intermediate data generated by the controller in processing the echo signals to yield the ultrasound image. In some embodiments the intermediate data comprises at least one of line-by-line RF data, Doppler data, and filtered data.

Another example aspect of the invention provides a method for presenting ultrasound images for review. The method comprises: at a review and imaging system retrieving ultrasound data including image data obtained by an ultrasound machine using user settings and additional data, the additional data including one or more of: data obtained using settings different from the user settings; and data from a stage of an image processing chain of the ultrasound machine upstream from the image data; displaying the image data on a display of the review and imaging system; receiving input of review settings different from the user settings by way of a user interface of the review and imaging system; and, based on the review settings, select from and/or process the additional data to yield a review image and displaying the review image on the display.

The method optionally processes the additional data to determine a set of available review settings and making the available review settings available for selection by way of the user interface. The review settings may comprise one or more of:
 an imaging depth different from an imaging depth specified in the user settings;
 a transmit focus different from a transmit focus specified in the user settings;
 a gain;
 a transmit frequency; and
 an apodization function.

Further aspects of the invention and features of example embodiments are described in the following description and/or illustrated in the accompanying drawings.

BRIEF DESCRIPTION OF THE DRAWINGS

The appended drawings illustrate non-limiting example embodiments of the invention.

FIG. 17A is a table providing parameters and values for an ultrasound machine operating in an extended imaging mode according to an example embodiment of the invention.

FIG. 17B is another table providing parameters and values for an ultrasound machine operating in an extended imaging mode according to an example embodiment of the invention.

FIG. 17C is a table providing parameters, values, and settings for the type of data to be captured by an ultrasound machine operating in an extended imaging mode according to an example embodiment of the invention.

FIG. 19 is a table providing parameters, values, and settings for an ultrasound machine operating in extended volumetric imaging mode according to an example embodiment of the invention.

FIG. 21 is a table providing parameters, values, settings, and rules for an ultrasound machine operating in extended imaging mode according to an example embodiment of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
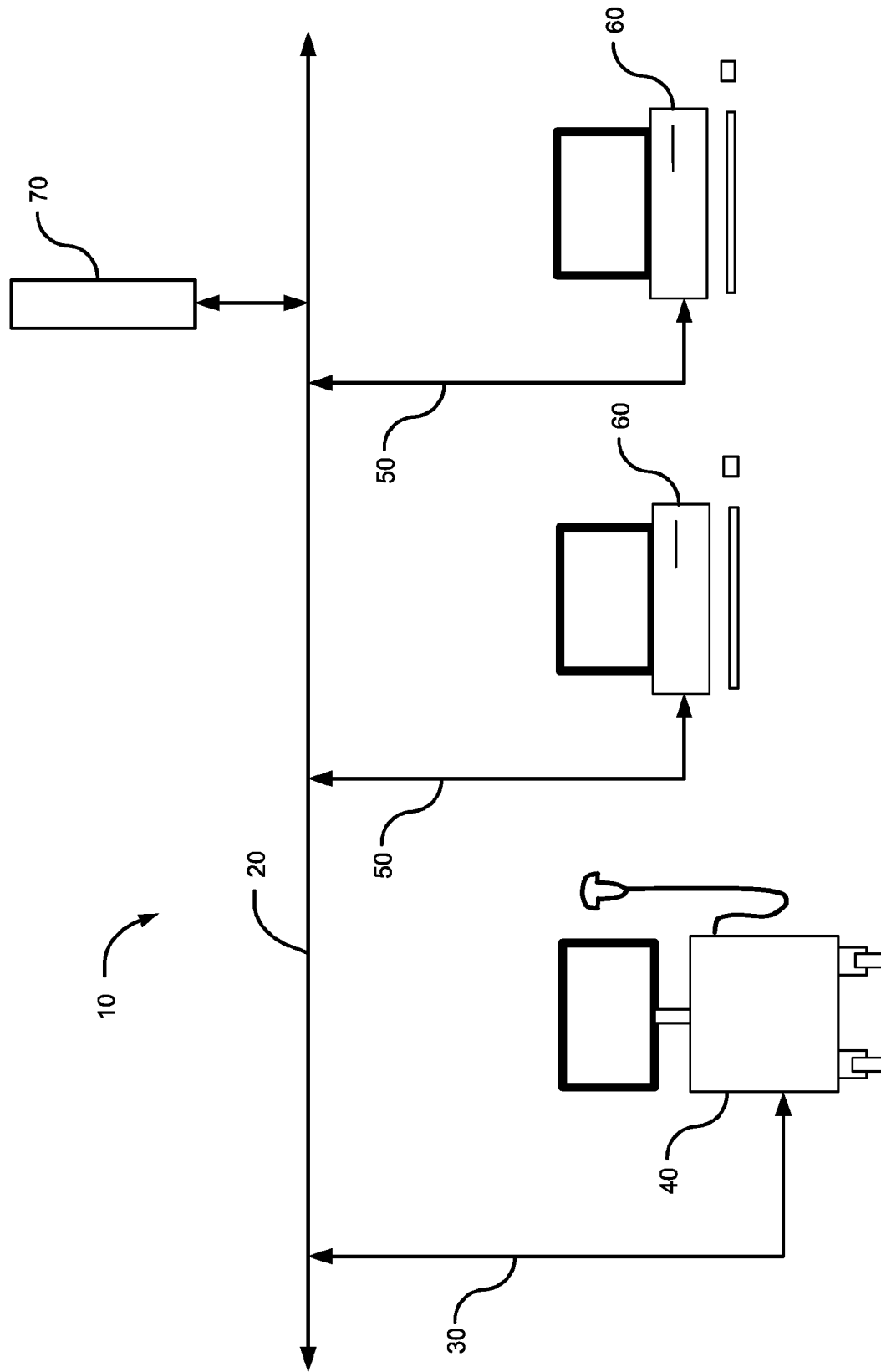
FIG. 1 is a schematic illustration of an ultrasound machine communicating with review stations through a network.

FIG. 1 is a schematic illustration of an imaging facility 10 comprising ultrasound machine 40 connected to a network 20 through a communications interface 30. More than one ultrasound machine 40 may be present in imaging facility 10. Ultrasound machine 40 may optionally be located in a dedicated scanning facility or room. A user (e.g. a sonographer) operates ultrasound machine 40 to acquire ultrasound images. The term "live imaging session" refers to the period when a patient is being scanned by ultrasound machine 40. During the live imaging session data is "acquired", "captured" and "stored". Reviewers (e.g. doctors or other qualified personnel) who can interpret the ultrasound images do not need to be present during the live imaging session.

Ultrasound images can be stored locally within an "exam" folder in ultrasound machine 40. Other information (e.g. information about the patient, system settings, scan settings, etc.) may also be stored within the exam folder. The images and other information can be transferred to a digital image storage and archival system 70. The transfer of information (image data, patient information, etc.) from ultrasound machine 40 to the storage and archival system may be performed over an available data communication channel using any suitable data format(s).

For example, the Digital Imaging and Communications in Medicine (DICOM) standard provides data formats and communications protocols useful for transferring and storing images and other information. The DICOM standard can be used to communicate images and other information regardless of the specific hardware configurations that created the information or the specific hardware used to interpret the information. Typically, images and other information are encoded in the DICOM format by the ultrasound machine.

Ultrasound images that are acquired and captured by ultrasound machine 40 can be reviewed later by a reviewer at review station 60. Review station 60 may be physically located near to or away from ultrasound machine 40. Review station 60 may connect to network 20 through wired or wireless communication protocol 50. The user who operates ultrasound machine 40 and the reviewer who reviews images at review station 60 could optionally be the same person.

The Ultrasound Machine

Figure 2:
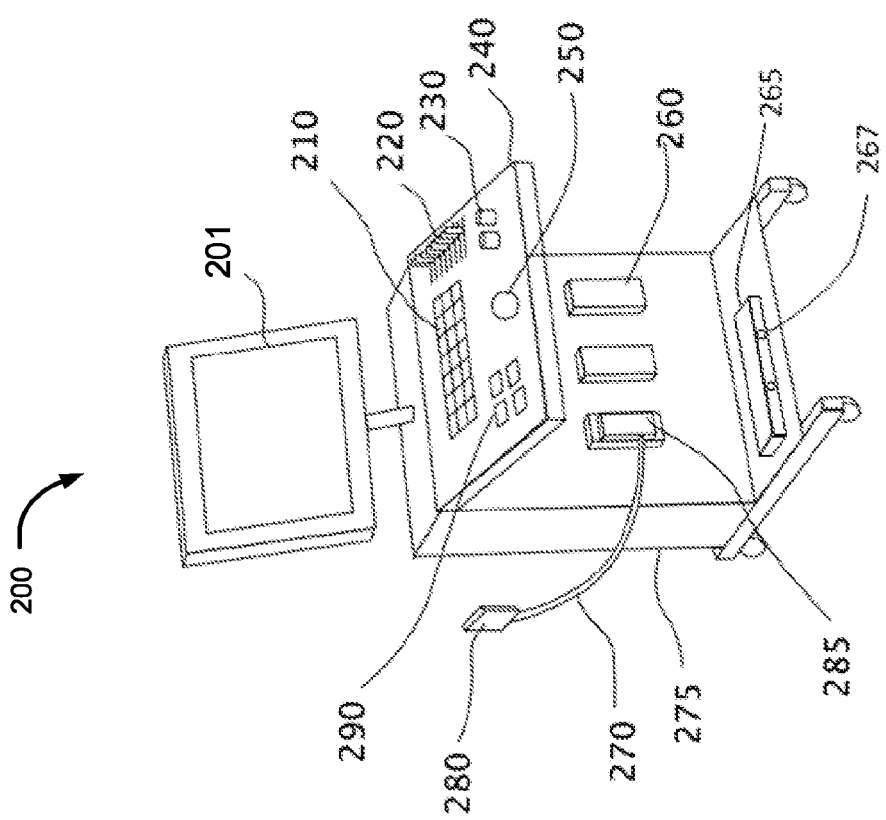
FIG. 2 is a perspective view of an ultrasound machine according to an example embodiment.

FIG. 2 is a perspective view of an example diagnostic ultrasound machine 200.

Ultrasound machine 200 may comprise display monitor 201, an ultrasound keyboard 240, at least one transducer 280, and a main body 275 which supports one or more transducer connectors 260 (only one connector 260 is labeled in FIG. 2). Transducer 280 may be coupled via a transducer cable 270 to a transducer connector 285 that plugs into one of the transducer connectors 260. In operation, ultrasound machine 200 drives transducer 280 to transmit acoustic energy into a target and receive reflected energy from interfaces within the target. Ultrasound machine 200 is configured to generate an image of the target by processing data characterizing the reflected energy. Ultrasound machine 200 may display the image of the target on monitor 201. Transducer 280 may comprise different heads for different types of ultrasound exams.

A user can interact with ultrasound machine 200 using controls provided by ultrasound keyboard 240. Different models of ultrasound machines may have different arrangements of and/or different selections of controls. Controls may be provided by physical components and/or by means of software and/or firmware. Non-limiting examples of controls include: switches (such as toggle switches, pushbuttons, radio buttons, or the like); rotary knobs and sliders having discrete or continuously adjustable outputs; pointing devices (such as trackballs, joysticks, stylus interfaces, mice, touch panels, touch screens); command line interfaces; keyboards, soft keys, etc. In the example of FIG. 2, ultrasound keyboard 240 comprises the following controls: a trackball 250, a QWERTY keyboard 210, one or several knobs 230, one or several push buttons 290, and time gain compensation (TGC) sliders 220.

Different functions can be assigned to different controls. Each control may possess a unique function. Alternatively, a user may customize the controls to provide different functions in different situations according to the user's preferences. Examples of functions that may be assigned to controls include, but are not limited to: setting the master gain in order to adjust image brightness, selecting one of a variety of different imaging modes (e.g. flow-mode, pulse wave mode), etc. Through the controls of ultrasound machine 200, a user may select a desired mode of operation, obtain images of a patient, view the images on monitor 201, and/or modify parameters that affect image quality.

Image quality may be affected, for example, by one or more of: increasing or decreasing the gain, changing filter settings of various filters that are applied along the signal path, changing post-processing maps (e.g. to achieve a specific aesthetic look of the image), changing the transmit and/or receive frequency (to choose between resolution and penetration), etc.

Variables that affect acquired ultrasound images can be referred to as "parameters". The inputs parameters can take are referred to as "values" or "settings" interchangeably. However, "values" may tend to refer to numeric inputs (e.g. gain or brightness levels) while "settings" may tend to refer to non-numeric inputs (e.g. different modes of operation). Different models of ultrasound machines may operate according to different sets of parameters and/or different available settings for the parameters. Most ultrasound machines allow a user to customize and set parameters such as gain, frequency, transmit focal range, transmit delays, receive delays, aperture size, apodization, filter selections, etc.

By adjusting the settings or values of one or multiple parameters through controls provided by ultrasound keyboard 240, a user has extensive ability to optimize the quality of the image that is displayed on monitor 201 of ultrasound machine 200. Once the user has optimized the desired image, the user may store the image as a still image and/or a cine loop by actuating a "capture" and/or "Cine" control. These images may be transferred to a digital image storage and/or archival system using known communication protocols. In some embodiments, a user can scroll through images after they have been stored in ultrasound machine 200 and/or set the size and location of pan boxes that help define regions of interest chosen by the user. These functions may be performed, for example, using trackball 250.

Figure 3:
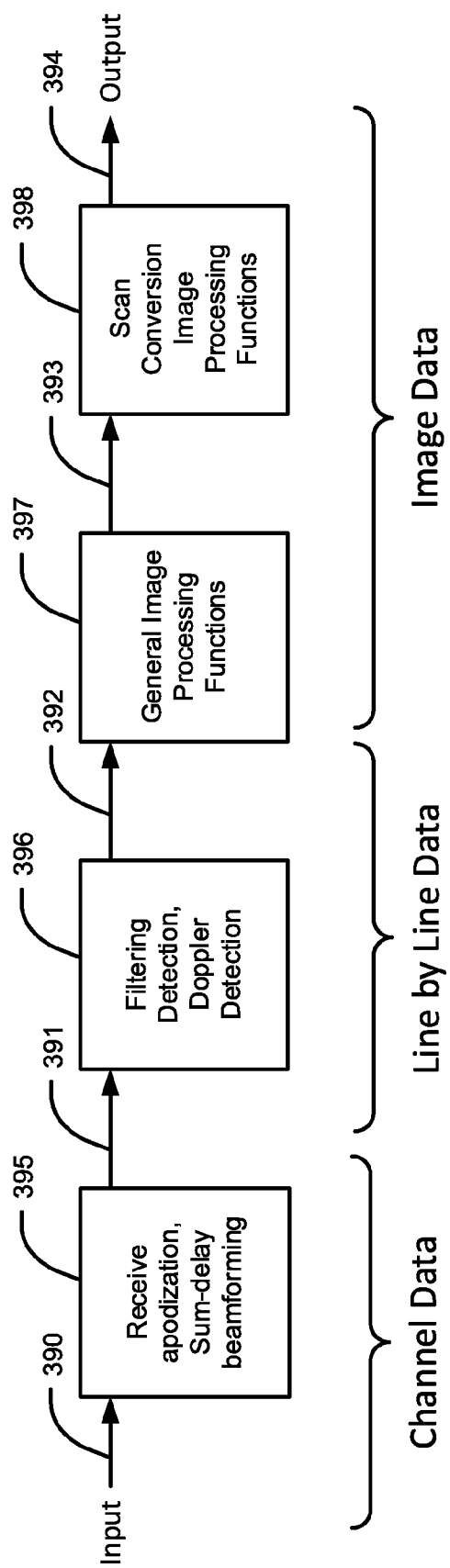
FIG. 3 is a functional flow diagram showing an imaging signal processing chain in an ultrasound machine according to an example embodiment.

FIG. 3 is a functional flow diagram showing an imaging signal processing chain in a typical ultrasound machine. The types of data that exist within an ultrasound machine may include but are not limited to: channel-by-channel RF data 390, summed line-by-line RF data 391, detected line-by-line data 392, pre-scan converted image data 393, and post scan-converted image data 394. These types of data can be collectively called "ultrasound data".

Processes 395, 396, 397 and 398 are non-limiting examples of some of the signal processing (e.g. processes 395, 396) and image processing (e.g. processes 397, 398) operations that may be performed on ultrasound signals within an ultrasound machine. Sum-delay-beamforming process 395 may be performed by summing channel-by-channel data 390, after applying the appropriate time delay value to each channel being summed, such that the ultrasound signal is in focus for all depth values. Filtering detection and/or Doppler detection (process 396 in FIG. 3) can be performed on line-by-line RF data 391 to produce line-by-line detected data 392. Line-by-line detected data is transformed into an image format in process 397. Pre-scan converted image data 393 is the output of process 397 and may, for example, comprise a 2D or a 3D matrix array. Finally, pre-scan-converted image data 393 is converted to scan-converted data 394. Scan-converted data 394 is the final product of the imaging process illustrated in FIG. 3. Scan-converted data 394 may be referred to as "display data". Scan-converted data 394 may be stored in the ultrasound machine, displayed on a monitor and/or transferred to other systems.

Some embodiments of the invention allow pre-scan converted image data 393 and/or detected line-by-line data 392 to be stored at an ultrasound machine. The data stored on the ultrasound machine can be later transferred to a digital image storage archival system and/or the local storage memory module on a review and imaging system. Some embodiments allow pre-scan converted image data 393 and/or detected line-by-line data 392 to be transferred to an external storage or display directly.

Figure 4:
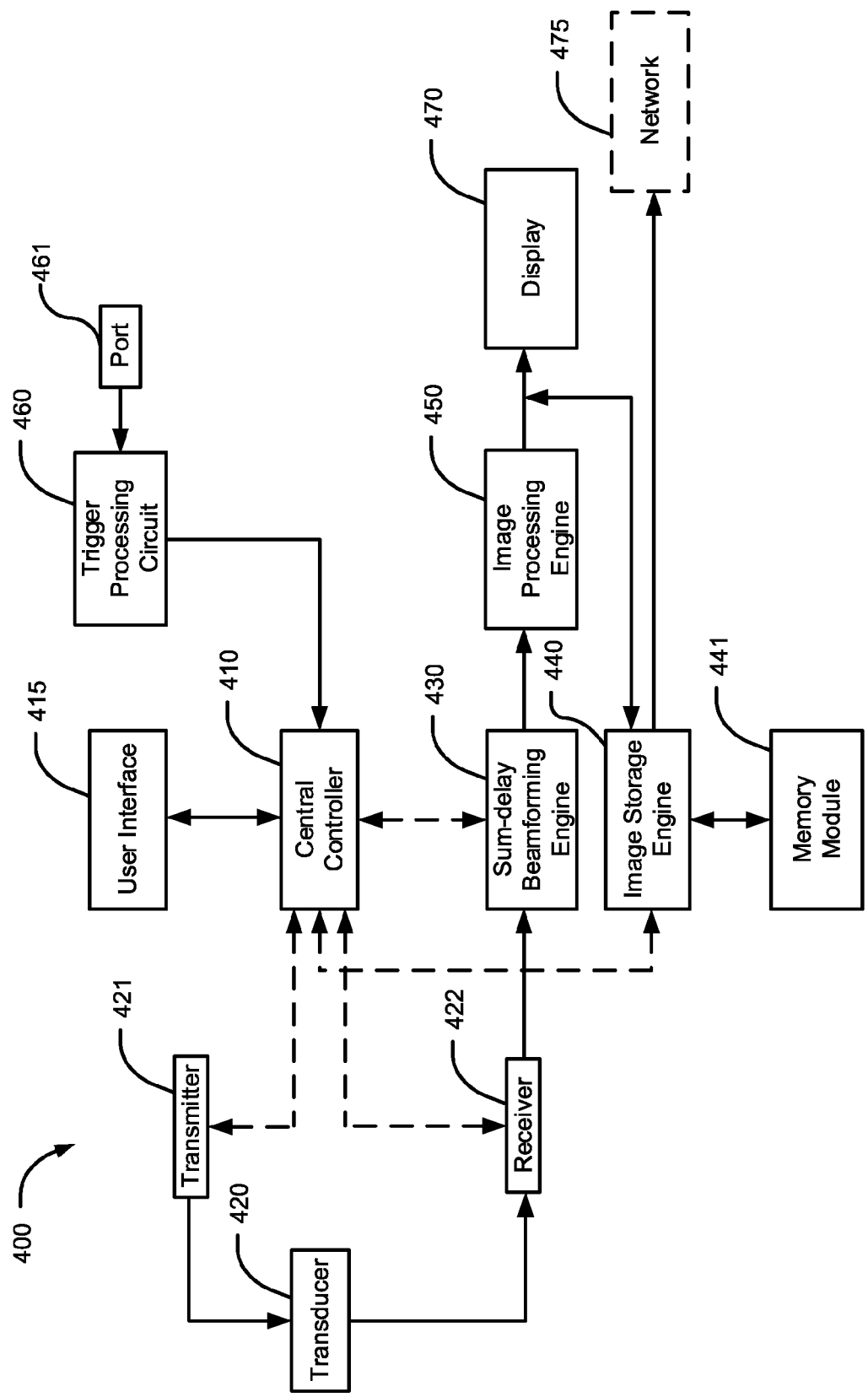
FIG. 4 is a block diagram of an ultrasound machine capable of communicating with a network according to an example embodiment.
Figure 5:
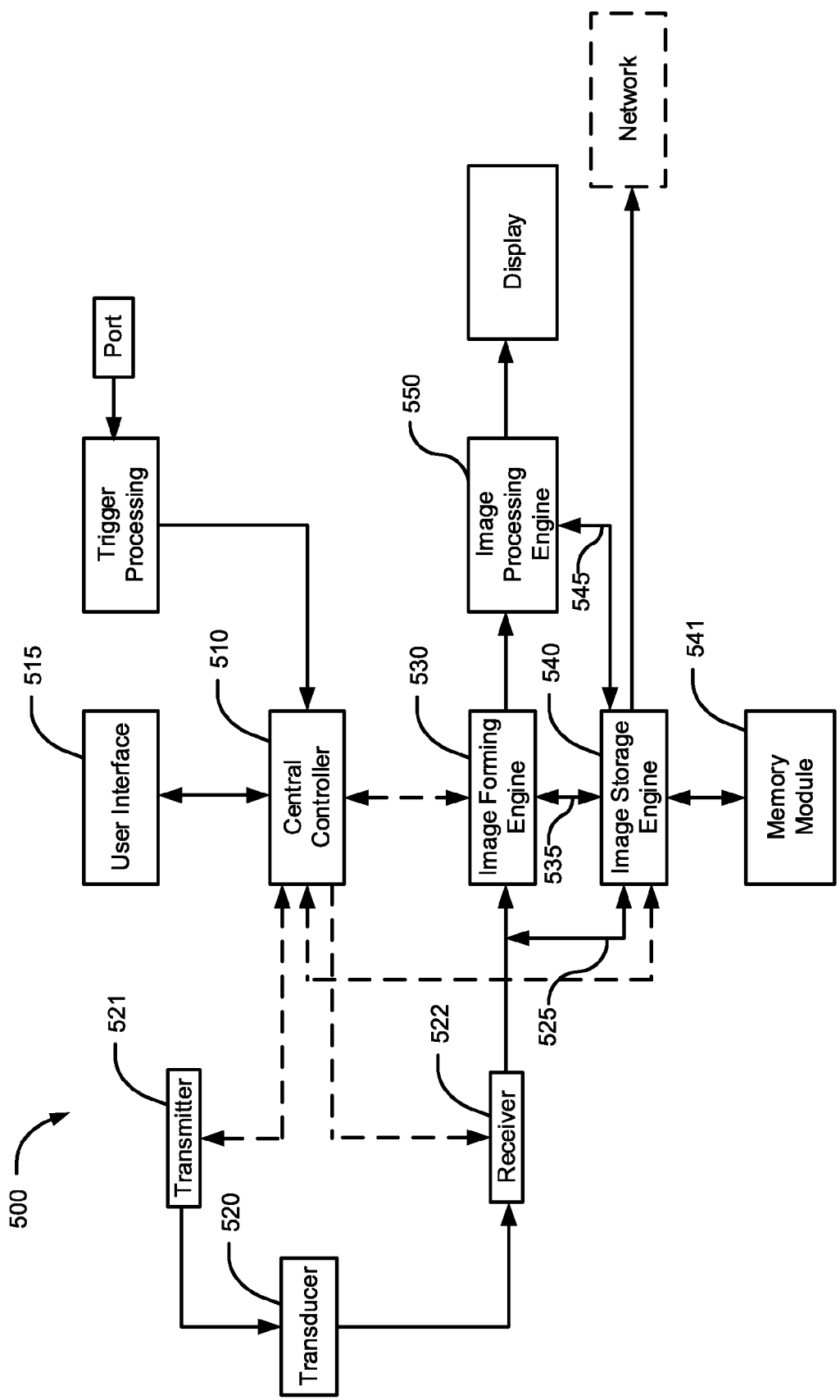
FIG. 5 is a block diagram of an ultrasound machine having alternative architecture according to an example embodiment.

FIGS. 4 and 5 are block diagrams of ultrasound machines 400, 500 according to non-limiting example embodiments of the invention. Ultrasound machine 400 or 500 may have any suitable features of design construction and/or operation in combination with features which facilitate the provision of additional data to a review and imaging station as described herein. For example, ultrasound machine 400 or 500 may incorporate features of any known ultrasound machines and/or features illustrated in FIG. 2 or 3 in any suitable combinations.

Ultrasound machines according to the present invention may generate ultrasound images using any known technology. For example an ultrasound machine may generate images using any of sum-delay beamforming, synthetic aperture imaging, algorithms that combine echo data channel by channel to generate images on a pixel-by-pixel basis and/or other image creation/image processing algorithms. The example ultrasound machine 400 illustrated in FIG. 4 applies sum-delay beamforming.

A user may operate ultrasound machine 400 by way of user interface 415. User interface 415 may comprise a graphic user interface, a voice-based user interface, a text-based user interface, etc. User Interface 415 may be a part of display 470, or a separate individual module.

In ultrasound machine 400, controller 410 sends control signals (dashed lines in FIG. 4) to transmitter 421, receiver 422, sum-delay beamforming engine 430, and image storage engine 440. Transmitter 421 may comprise transmitter circuits, while receiver 422 may comprise receiver circuits.

Controller 410 controls the timing of the various components of ultrasound machine 400 (e.g. transducer 420, sum-delay beamforming engine 430, etc.) through the control signals. Controller 410 also sends the settings or values of various parameters to various components of ultrasound machine 400.

Transducer 420 transmits and receives ultrasound signals. Transducer 420 may comprise a transducer array. During a live imaging session, transmitter 421 may cause transducer 420 to send energy into a body to be imaged. Receiver 422 may then receive from transducer 420 echo signals reflected from interfaces within the body. Transmitter 421 may comprise plural transmit channels, while receiver 422 may comprise plural receive channels. In some embodiments, electrical excitation with appropriate timing is sent through a transmit channel of transmitter 421 to one or more corresponding elements of transducer 420. In some embodiments, receiver 422 amplifies and/or digitizes the signals received at the receive channels from corresponding elements of transducer 420.

Sum-delay beamforming engine 430 receives data representing echo signals from channels of receiver 422 and performs sum-delay beamforming on the data to achieve dynamic receive focusing Image processing engine 450 receives data from sum-delay beamforming engine 430 and performs further signal processing. Example signal processing techniques that may be performed by image processing engine 450 include, but are not limited to: filtering, combining signals, thresholding, log compression, remapping of gray values, etc.

In some embodiments, a user may cause ultrasound machine 400 to capture or store images produced by image processing engine 450 in image storage engine 440. Capture and storage may occur in response to a user activating a capture control. The capture control may be activated through user interface 415. Image storage engine 440 is operable to store the images produced by image processing engine 450 for further use. Image storage engine 440 may be connected to a memory module 441. Memory module 441 may provide greater storage capacity and/or comprise non-volatile memory. Image storage engine 440 is also operable to transfer stored images to other devices through network 475.

Ultrasound machine 400 may further comprise a trigger processing circuit 460 to receive physiological signals. In some example embodiments, an electrocardiogram (ECG) machine is connected to trigger processing circuit 460 through port 461. Trigger processing circuit 460 may process received physiological signals such as ECG signals in many ways including but not limited to: applying filters to remove unwanted signal components or to smooth the signal. These filtering steps may reduce triggering due to spurious noise. A triggering circuit or system may also be included within trigger processing circuit 460. The triggering circuit may generate triggers in response to triggering events indicated in the received physiological signal. These triggers may be routed to controller 410 within ultrasound machine 400. If a triggering event occurs, trigger processing circuit 460 will receive an input through port 461 and transmit a signal to controller 410. Controller 410 may be programmed to start imaging when such a signal is received from trigger processing circuit 460. Controller 410 may be further programmed to image only for a certain set amount of time that may itself be programmable.

FIG. 5 is a block diagram of an ultrasound machine 500 according to another example embodiment. Ultrasound machine 500 is similar to ultrasound machine 400 (see FIG. 4), except that sum-delay beamforming engine 430 is replaced with an image forming engine 530 that may form images using any suitable image forming technique(s).

Data Acquisition on the Ultrasound Machine

Ultrasound machines according to some embodiments are configured to make additional data available to a review and imaging system. "Additional data" goes beyond the image data for a captured image. Such "additional data" may include data from earlier in the image processing chain and/or data obtained automatically by the ultrasound machine using settings different from the current settings used to obtain the captured image and/or data that records parameters and related settings associated with the image that is being captured. In some embodiments the additional data is or includes data that is not used in creating an image being displayed at the ultrasound machine. For example the additional data may be generated by detecting echo signals from a transmission of ultrasound energy generated specifically for creating the additional data. Where the additional data comprises data from a stage of the image processing chain upstream from scan-converted image data it is optionally possible for the ultrasound machine to suppress additional processing of the additional data. Additional data may comprise data that would not be stored by a conventional ultrasound machine operating under current settings and/or data that would not be obtained or created in an ultrasound machine operating under the current settings.

For example, ultrasound machine 500 has an architecture that permits data present at one or more signal processing stages upstream from the final scan-converted image to be made available to a review and imaging system. In the illustrated embodiment ultrasound machine 500 comprises connection 525 that allows channel-by-channel RF data digitized by receiver 522 to be captured and stored directly in image storage engine 540. Ultrasound machine 500 may also comprise connection 535 that allows data generated by image forming engine 530 (e.g. line-by-line RF data, Doppler data, filtered data, etc.) to be captured and stored directly in image storage engine 540. Ultrasound machine 540 may further comprise connection 545 that allows various types of line-by-line data (e.g. line-by-line pre-scan-converted data, line-by-line post-scan-converted data, pre-scan-converted image data, post-scan-converted image data, etc.) to be captured and stored in image storage engine 540.

In some embodiments, parameters and related inputs associated with the image that is being captured are stored by ultrasound machine 500. Such stored inputs (e.g. values and settings) may be applied to reconstruct images and/or create new images from stored ultrasound data at a review and imaging system.

Different ultrasound machines may be configured to store different types of data. For example, ultrasound machine 400 stores and/or displays scan-converted images or output images of an image processing chain, while ultrasound machine 500 can be configured to store and/or display one or more additional data types associated with the ultrasound images. Storing data that exist earlier in the imaging processing chain may permit more flexibility in forming new images or adjusting the quality of images at a review and imaging system.

Ultrasound machine 500 may comprise a data store function capable of storing any post scan-converted data and/or additional data and/or any combination of available data. The additional data that may be stored include, but are not limited to:

- data of one or more types present in an ultrasound machine upstream of post scan-converted data;
- data specifying settings used to post or pre scan-converted ultrasound data;
- additional data acquired using settings different from those selected by a user of an ultrasound machine for a selected ultrasound image;
- data specifying or identifying data-processing algorithms used by the ultrasound machine;
- data specifying one or more of the controls provided by the ultrasound machine, available settings for the parameters set by the controls, and an arrangement of controls of the ultrasound machine.

The particular data that is captured and stored when the data store function is activated may be specified, for example by:

one or more presets in the ultrasound machine selectable by a user of the ultrasound machine;

a rule that identifies settings for acquisition of additional data based upon settings selected by a user of the ultrasound machine and/or features of acquired image data and/or other features of a state of the ultrasound machine and/or a model or type of the ultrasound machine and/or a type of transducer being used to acquire ultrasound data;

specific additional data specified by a configuration of the ultrasound machine.

The additional data may be of various types; for example, the additional data may include one or more of:

one or more types of Radio-frequency (RF) data. The term "RF data" can include but is not limited to base band in-phase and quadrature (IQ) data and/or intermediate frequency (IF) data. The ultrasound machine architecture largely determines the type of RF data that can be stored. It is also to be noted that RF data can include data generated from various imaging modes such as but not limited to B-mode, flow mode, pulsed wave Doppler mode, strain mode, contrast imaging mode, tissue harmonic mode and others.

Pre-scan converted detected data

Pre-scan converted image data and

Scan-converted or display data.

RF data may include channel-by-channel RF data or beamformed line-by-line RF data. RF data may be obtained by digitizing each transducer element at an appropriate sampling frequency. Sampling frequencies typically range from 40 MHz to 60 MHz. Other sampling frequencies may also be used as dictated by the architecture of the ultrasound machine. The architecture of ultrasound machine 500 allows the capture and storage of RF data.

Channel-by-channel RF data may be useful in cases where a synthetic aperture type of imaging method is utilized within the ultrasound machine during the live imaging session. In synthetic aperture imaging, the ultrasound echo data received at receiver 522 after every transmission may be digitized and stored locally in memory module 541 within ultrasound machine 500.

A user may trigger the storage of channel-by-channel data or other additional data by actuating a control (e.g. a "data store" control) at ultrasound machine 500. The "data store" control may be activated through user interface 515. In some embodiments, the channel-by-channel RF data and/or other additional data may be stored automatically.

Line-by-line RF data (rather than channel-by-channel data) is more appropriate to store and transfer in cases where delay-sum beamforming methods are used within the ultrasound machine during the live imaging session. Line-by-line RF data may be formed within image forming engine 540. The "lines" correspond to steering directions of the receive beamformer. A user may initiate the data store function to store line-by-line RF data, or the data store function may be initiated automatically.

Depending on the architecture of the ultrasound machine, line-by-line RF data may be generated with a synthetic aperture type of imaging method. Synthetic beamforming may be implemented in process 395 (see FIG. 3).

In some embodiments, RF data is stored for future use. The stored RF data may have minimal or no filtering (or other processing). A review and imaging system as described herein may permit a reviewer to select filters (or other processing) to be applied to the RF data. Applying filters and/or other processing may thereby improve the quality of the images generated from the RF data. In some embodiments, RF data with some filtering (e.g. anti-aliasing filters before analog to digital conversion) is stored on or otherwise made available to a review and imaging system for future use.

Ultrasound Machine: Extended Imaging Mode

In some embodiments, an ultrasound machine is configured to automatically acquire, capture and store additional data. Such additional data may be obtained and stored, for example, when a user activates a data store function. The additional data stored may include data of one or more of the types described above. The nature of and amount of additional data stored may depend on the ultrasound machine configuration (including hardware configuration, processing steps and/or algorithms) and/or settings selected by a user for parameters that affect what additional data is available and/or what additional data is to be made available.

In extended imaging mode, the ultrasound machine is programmed to automatically change the system settings, transmit and receive ultrasound energy with the modified system settings, and store the ultrasound signals and other data generated as a result of the transmit operation, the receive operation and/or other signal and image processing steps. Modified system settings may be determined automatically based on system settings selected by a user of the ultrasound machine. Extended imaging modes that generate scan-converted data may optionally be implemented in firmware for an ultrasound machine. Some available ultrasound machines can support such extended imaging modes without requiring hardware modification.

Modified system settings can include but are not limited to one or more of:

change of depth;

change of transmit frequency;

change of transmit focus;

change of transmit apodization function;

change of transmit aperture;

change of receiver aperture;

change of receive apodization function; and change of beamforming function;

Referring to the change of depth modification as an example, the ultrasound machine may be configured to automatically store two or more sets of data (each set at a specific imaging depth) upon activation of the data store function. At least one of the sets of data may have a setting for the depth parameter selected by a user of the ultrasound machine. One or more additional sets of data may be acquired using other settings for the depth parameter. The other settings for the depth parameter may be based on the setting selected by the user (e.g. one or more settings deeper than selected by the user and/or one or more settings less deep than the setting selected by the user, one setting a certain multiple of the setting selected by the user—the certain multiple may be greater than or less than one, one setting a certain number of steps deeper than or less deep than the setting selected by the user, etc.) and/or specified independently.

Thus, in an abdominal examination example, a user may instruct the ultrasound machine to capture and store 5 seconds worth of data at 70 mm depth at a frequency of 2 MHz and transmit focus at 50 mm. The ultrasound machine may, in response to the instructions, capture additional data including but not limited to 5 seconds worth of data at 100 mm depth at the same frequency of 2 MHz and transmit focus at 50 mm, and 5 seconds worth of data at 150 mm depth also at the same frequency of 2 MHz and transmit focus at 50 mm.

Other system settings may also be modified in the same way. For example, in a vascular exam, a user may instruct the ultrasound machine to capture 5 seconds worth of data at a frequency of 7 MHz at an imaging depth of 40 mm with a transmit focus at 20 mm. The ultrasound machine may, in response to the instruction, capture additional 5 seconds worth of data at 10 MHz also at an imaging depth of 40 mm with a transmit focus at 20 mm may be stored. The ultrasound machine can be tuned so that multiple system settings are swept and automatically captured in an ultrasound exam.

In some embodiments, an ultrasound machine has a user interface (e.g. ultrasound keyboard 240 in FIG. 2) that allows a user to specify additional system settings that will determine what additional data the ultrasound machine will acquire in the extended imaging mode. For example, such additional system settings may specify for each of one or more sets of additional data, parameters and values to be used to acquire the additional data. In some embodiments, the ultrasound machine may generate the parameters and values for each set of additional data by modifying the parameters and values being used by the user according to the corresponding set of additional system settings. Each set of additional system settings may specify specific values for one or more parameter and settings that override settings selected by the user and/or rules for modifying the parameters and settings selected by the user (e.g. increase depth by one step or decrease frequency by a predetermined amount).

The decision of what data and how much data to collect may be informed by several factors. In some cases, this decision may be informed by the reviewer's preferences. Typically the user may have some knowledge about who the reviewer is and what he or she may prefer. This knowledge may be used to guide the decision as to what data to collect. Selection of what data and/or how much data to collect is automated in some embodiments. For example the system may be configured to set what data and how much data to collect based on identification of the reviewer. In some other cases, it may be possible that different reviewers are called upon to review the exam. In this case, the user may collect data to accommodate the preferences of the different reviewers.

To illustrate this with an example, reviewer A may prefer to examine ultrasound images at multiple depths but the same frequency. This may help ensure that deviances from a normal healthy state of the tissue are not missed, especially if it occurs at a deeper depth within the body. Reviewer B may want to see multiple frequencies at the same depth since the information content of the image changes with imaging frequency. Higher imaging frequencies lead to better resolved images and higher contrast resolution at the expense of lower signal-to-noise ratio. Thus, small lesions are typically examined with a higher frequency, provided that adequate signal-to-noise ratio is present. However, some reviewers prefer to look at lesions at different frequencies. In some embodiments, the review and imaging system may include analysis capabilities that requires certain type of data such as but not limited to data at different frequencies. If this is known a priori, the data collection process can be configured to accommodate this need. As an example, some analysis algorithms (e.g. volume estimation or size estimation of an organ) may require data at different frequencies and may also require data at multiple depths so that an entire organ or as much of the organ as possible is imaged.

In all these cases, the ultrasound machine may be programmed to change the system settings automatically after one set of data with its associated system setting has been captured and stored. The sequence of system settings and the duration of acquisition with each system setting may be specified a priori before the live imaging session or during the live imaging session. As indicated earlier, multiple parameters and their values can be specified within each system setting. Thus between each system setting, multiple parameters can be modified.

For example, data can be acquired at 40 mm at 10 MHz in one system setting and 50 mm at 7 MHz in the next system setting. The sequence of system settings that the ultrasound machine systematically goes through in this extended imaging mode may be specified in a table. This table may be generated a priori or interactively at different time instances relative to the time a patient is being scanned. For example, the table may be generated off-line on a computer before scanning a patient and/or during the time a patient is being scanned. Once a table is generated, a controller (e.g. controller 510 in FIG. 5) may interpret the table and provide the appropriate timing, control data or other information to the various blocks within the ultrasound machine so that data acquisition, capture and other tasks are performed at appropriate times.

FIG. 17A is an example table providing parameters and values that may be input to an ultrasound machine operating in an extended imaging mode. In some embodiments, a user may input multiple sets of values at different time periods. In other embodiments, a user only needs to input one set of values at a single time period and the ultrasound machine automatically generates the other sets of values.

As seen in FIG. 17A, the first period lasts for 5 s as the ultrasound machine images a patient with a frequency of 2 MHz at an imaging depth of 70 mm and with the transmit focus at 50 mm. The second and third time periods also last for 5 s, but the ultrasound machine images the patient at an imaging depth of 100 mm and 150 mm respectively with other parameters fixed. The sequence provided in FIG. 17A may be useful for procedures like an abdominal examination.

FIG. 17B is another table providing parameters and values that may be input to an ultrasound machine operating in extended imaging mode according to an example embodiment of the invention. In FIG. 17B, the first period lasts for 5 s as the ultrasound machine images a patient with a frequency of 7 MHz at a fixed imaging depth of 70 mm and fixed transmit focus at 50 mm. The second time period also lasts for 5 s, but the ultrasound machine images the patient with a frequency of 10 MHz. The sequence provided in FIG. 17A may be useful for procedures like a vascular examination.

Although FIG. 17A and FIG. 17B specify values for only a few parameters (frequency, depth and location of transmit depth). The tables in FIG. 17A and FIG. 17B may comprise more or fewer parameters, and such parameters may include without limitation any one or more of front end gain, back end gain, filters applied prior to or after magnitude detection, transmit and receive apodization, etc. The tables may also comprise more or less time periods. Each time period may alter the values of any number of parameters.

An extended imaging mode may be implemented in many ways. In one variation, the table (e.g. FIG. 17A) does not need to contain all the parameters required for forming images. In these instances, the ultrasound imaging system may automatically select values for unspecified parameters. For example the ultrasound machine may use the same parameter settings as the ones previously used by the system. For example, the front-end gain is not specified in FIG. 17. So when the ultrasound machine images with the settings for the first time period, the front-end gain setting may be identical to the one the system was using just prior to activation of the extended imaging mode. If the front-end gain was specified as 4 dB just prior to activation of the extended imaging mode, the gain used post activation may also be 4 dB. This concept may be extended to multiple or all parameters that are needed to generate an image.

In another variation, rules established within the ultrasound machine may be used to automatically set unspecified parameters. These rules may be established by software programs that are responsible for the ultrasound machine operation, and/or other mechanisms. For example, the front-end gain parameter may be set automatically based on a frequency parameter. For example, a front-end gain of 6 dB may be associated with a frequency of 10 MHz. This association may be done a priori or interactively.

Thus, if the front-end gain was 4 dB prior to activation of the extended imaging mode and the table did not contain a specific entry for gain (as shown in FIG. 17B), then 4 dB front-end gain may be utilized for the first imaging period upon entering the extended imaging mode. However, upon entering time period 2 when the frequency is adjusted to 10 MHz, a front-end gain of 6 dB may be utilized through another rule established elsewhere in the system.

In another variation, the time periods may be initiated by triggering events. For example, a patient may be coupled to a machine recording the patient's ECG, and the ECG may be input to a trigger processing circuit (e.g. trigger processing circuit 460 in FIG. 4) in the ultrasound machine. After activation of the extended imaging mode, the time periods may be further activated or initiated when certain events (e.g. peak of the QRS complex, etc.) occur within the ECG trace. After the first imaging period has concluded, the second time period may not commence until the same event recurs and/or another event occurs in the ECG trace. This mode may be beneficial in situations when images are to be formed in the review and imaging system from multiple time periods.

In another variation, a set of commands that control what additional data will be obtained in the extended imaging mode may be associated with a particular reviewer or a particular patient or a particular referring physician, a particular sonographer etc. The ultrasound machine may select a set of commands based on information regarding a particular examination (e.g. who will be the reviewer or who is the referring physician) and then execute the commands to set up the extended imaging mode.

Upon entering the extended imaging mode, the ultrasound machine can be programmed to store one or multiple types of ultrasound data including but not limited to: RF data, pre-scan converted detected data, scan-converted or display data, etc. In some embodiments, the type of data captured can be specified in a table.

FIG. 17C is a table providing parameters, values, and settings for the type of data to be captured for an ultrasound machine operating in an extended imaging mode according to an example embodiment of the invention. In this example embodiment, both channel-by-channel RF data and scan converted data are collected for each time period. Although the types of data captured and stored are the same (e.g. channel-by-channel RF data, scan converted data), the imaging conditions are different (e.g. depth). As seen in FIG. 17C, an ultrasound machine according to an example implementation of the present invention operating in an extended imaging mode can provide the flexibility to specify the imaging conditions, the amount of time, and the type or types of data to be captured and stored (within the extended imaging mode).

Other ways for specifying what additional data will be acquired in an extended imaging mode include but are not limited to: providing a file containing values that define the additional data to be stored, setting controls, configuring the ultrasound machine (e.g. by firmware) to always acquire a certain types of data in the extended imaging mode, etc.

In some embodiments, the ultrasound machine provides feedback to the user to indicate the status of the data collection process while in the extended imaging mode. For example, the ultrasound machine may display the status of the data collection process on a display (e.g. display 201). The display may include information such as but not limited to the type of data being collected, how much of the data has been collected, how much more time is required to finish collecting the data etc. In some cases, the tables such as FIGS. 17A, 17B and 17C may be displayed. The row that is being utilized to collect data may be highlighted. The completion of data collection may also be indicated by a message such as "Data collection complete" or other audible, visual and/or tactile feedback signal.

Figure 18:
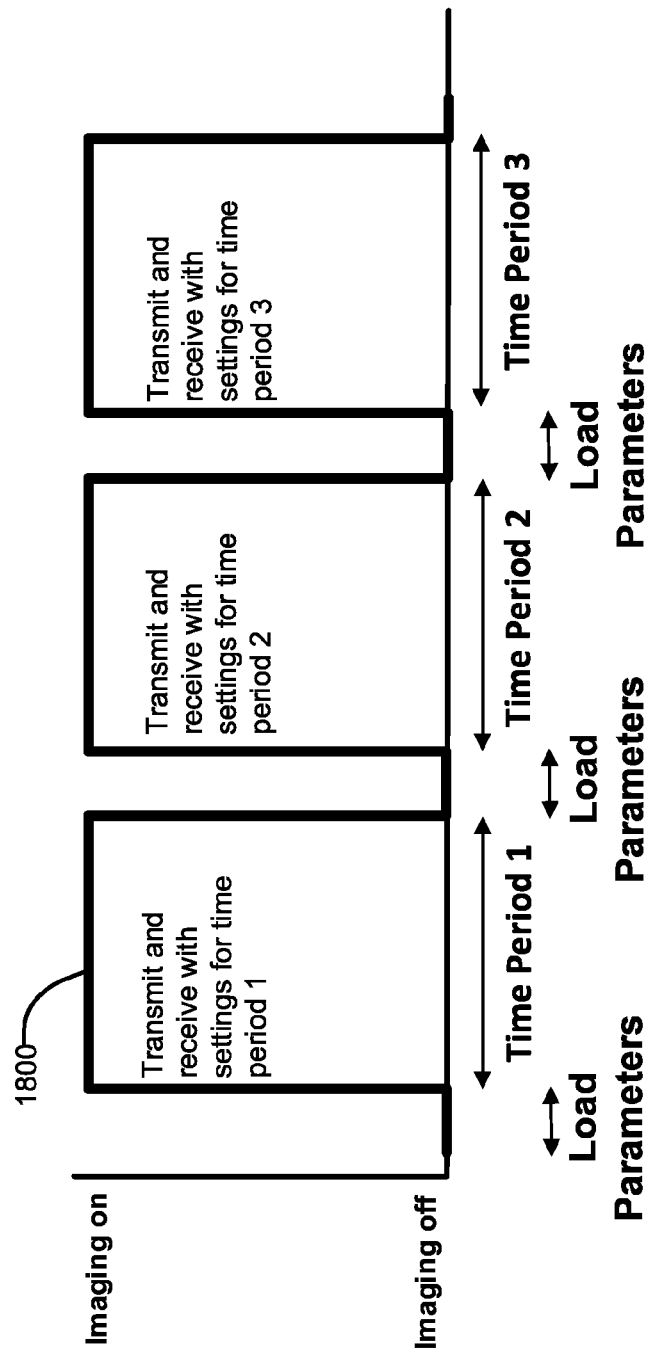
FIG. 18 is a timing diagram illustrating the sequence of events occurring within the ultrasound machine when the parameters and values in FIG. 17A are being utilized.

FIG. 18 is a timing diagram illustrating the sequence of events occurring within an ultrasound machine when the parameters and values in FIG. 17A are being utilized. When the extended imaging mode is activated, the ultrasound machine modifies the system settings as specified in FIG. 17A, and obtains images of the patient in the sequence and for the amount of time specified.

In FIG. 18, curve 1800 illustrates time periods when the ultrasound machine is imaging and time periods when the ultrasound machine in not imaging. During Time Period 1, the ultrasound machine images the patient with parameters and their values specified in the first time period of FIG. 17A. The ultrasound machine then loads the parameters and their values specified in the second time period of FIG. 17A before imaging the patient at Time Period 2. At Time Period 2, the ultrasound machine images the patient with modified settings based on the second set of data shown in FIG. 17A. After Time period 2 concludes, the parameters and their values specified in the third time period of FIG. 17A are loaded in the ultrasound machine. The ultrasound machine uses these values to image the patient again during Time Period 3.

In some embodiments, the time periods may not start until a triggering event occurs. For cardio exams, a triggering event may occur when the peak of the QRS complex is larger than a certain preset value. Although time periods start at regular intervals in FIG. 18, time periods may not start at regular intervals when trigger processing is used. Although the ECG is used as a triggering signal in this example, other signals such as but not limited to respiratory signals may also be used to trigger acquisition or storage of ultrasound images.

Extended Volumetric Imaging Mode

In a variation of the extended imaging mode, volumetric data can be obtained when a user activates the data store function. Similar to the extended imaging mode, the type of data captured may be one or more of the types described above (e.g. RF, pre-scan converted detected or scan-converted or display data), depending on the ultrasound machine configuration and system settings. Transducers that generate data suitable for the extended volumetric ultrasound data mode include but are not limited to 2D transducers, 1D transducers that can wobble, and 1D transducers that are able to rotate.

In the extended volumetric imaging mode, the ultrasound machine may be programmed to change the system settings automatically after each set of data has been stored. The sequence of settings and the time of acquisition for each setting may be specified a priori before the live imaging session or may be specified by the user during the live imaging session. Similar to the extended imaging mode described above, the settings within an ultrasound machine operating in extended volumetric imaging mode can be programmed so that data sets with different parameters and values may be acquired, stored and transferred.

FIG. 19 is a table providing example parameters, values, and settings for an ultrasound machine operating in extended volumetric imaging mode according to an example embodiment of the invention. In this case, the type of data to be captured is specified to be line-by-line pre-scan converted data. In this table, Time Period 1 lasts for 5 and the imaging frequency is 7 MHz at a depth of 40 mm, with a transmit focus at 20 mm. The elevation scan angle is chosen to be 5° and the azimuthal scan angle is chosen to be 10°. Time Period 2 also lasts for 5 s, but the imaging frequency is 10 MHz at an imaging depth of 30 mm (transmit focus still at 20 mm). In addition, the elevation scan angle in this case is set to 10° while the azimuthal scan angle remains at 10°. By capturing images at different scan angles and transferring them to the review and imaging system, a user can help a reviewer recreate 3D ultrasound images on a review and imaging system without rescanning a patient.

The Review Station

Figure 6:
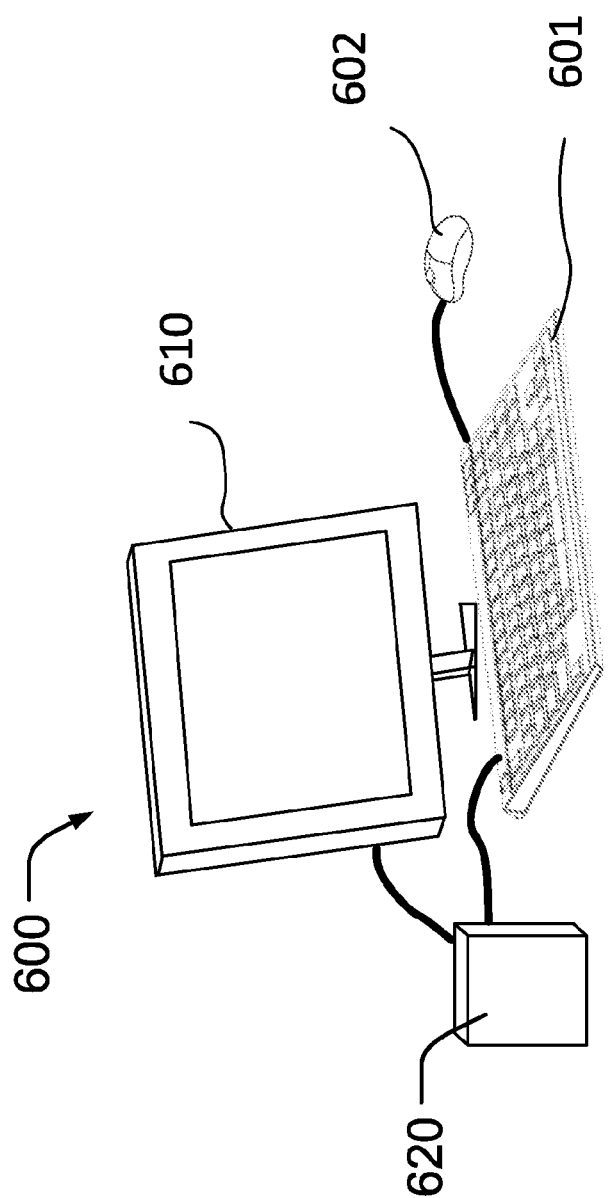
FIG. 6 is a perspective view illustrating a review station.

FIG. 6 is a perspective view of a review station 600 of a type that may be used as review station 60. Review station 600 may comprise keyboard 601, mouse 602, display 610, and computer 620 which runs software that allows a reviewer to select and display images for review. Review station 600 may be connected to a network, an ultrasound machine, and/or an external memory module (see e.g. FIG. 1). A reviewer can use review station 600 to view ultrasound images and make a diagnosis. Display 610 may comprise a monitor capable of displaying high resolutions. Computer 620 may run software that provides tools that enable the reviewer to efficiently display ultrasound images retrieved from an image storage and/or archival system (see FIG. 1) for review.

Review station 600 may comprise a number of controls through which the reviewer can view the images. These controls may be provided by keyboard 601, mouse 602, or other inputs (not shown). Examples of such controls include: controls that allow a reviewer to fast forward and rewind cine loops, controls that allow a reviewer to change the brightness and contrast of images, controls that allow a reviewer to perform measurements, quantification and calculation on ultrasound images, etc. By interacting with the images (e.g. performing measurements, calculations and quantifications), a reviewer may arrive at a diagnosis for a patient.

Measurements usually refer to the measurement of the size of an anatomical structure, while calculations usually refer to values derived from the measurements. For example, gestational age for a pregnant patient may be calculated based on measurements of the gestational sac diameter and the crown-rump length. A caliper tool may be placed on an image to measure the size of the anatomical structure. Quantification usually refers to more advanced calculations. For example, finding the ejection fraction, finding the stroke volume, or quantification of left ventricular function are quantification functions used for diagnosis of cardiac function.

The Review and Imaging System

Figure 7:
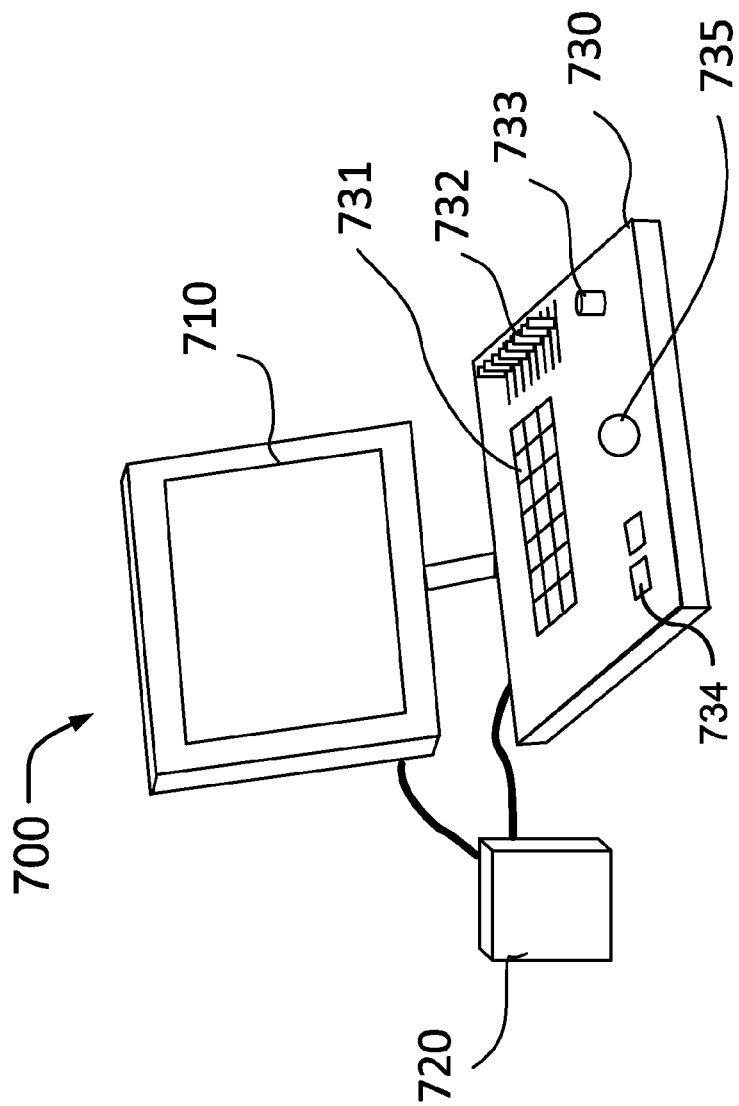
FIG. 7 is a perspective view illustrating a review and imaging system according to an example embodiment.

FIG. 7 is a perspective view of a review and imaging system 700 according to an example embodiment of the invention. A review and imaging system may incorporate any features of design construction and/or operation known for inclusion in review stations or any combinations of such features together with features as described herein for enhanced control of the processing and display of images and/or handling additional data.

Review and imaging system 700 comprises a display 710 driven by a computer 720. Review and imaging system 700 may provide controls that allow a much wider range of control over displayed images than is possible in review station 600. Such control is facilitated by the availability at review and imaging system 700 of additional data from earlier stages of an imaging processing chain of an ultrasound machine and/or additional data obtained using different settings of the ultrasound machine.

For example, review and imaging station 700 may include controls that allow a reviewer to change one or more of: imaging depth, imaging frequency, the location of transmit focus, the number of transmit foci within a sequential focus pattern, filters applied to radio-frequency data or the baseband domain. Such controls could not be provided in a review station 600 which receives only processed image data from an ultrasound machine.

In some embodiments, review and imaging system 700 comprises ultrasound keyboard 730. Ultrasound keyboard 730 may comprise, for example, a keypad 731, sliders 732, one or several knobs 733, one or several push buttons 734, and one or several trackballs 735. Ultrasound keyboard 730 may be similar to ultrasound keyboards found on ultrasound machines used to acquire ultrasound images (e.g. ultrasound keyboard 240 in FIG. 2). For example, ultrasound keyboard 730 may provide controls arranged in the same way as equivalent controls are provided on ultrasound keyboard 240. This configuration may work especially well when all the ultrasound machines used by the sonographers or technicians in a particular group or practice are the same. In a large practice or in a hospital, where ultrasound machines from various manufacturers may be in use, the ultrasound keyboard used for the review and imaging system may not necessarily be the same as those found in any one type of ultrasound machine although this configuration is not excluded. Ultrasound keyboard 730 need not have all of the controls found on a keyboard coupled to an ultrasound machine although that configuration is not excluded.

In some embodiments, review and imaging system 700 comprises image processing modules that process data formed in the earlier stages of the image processing chain of the ultrasound machine (e.g. pre-scan converted data, RF data, etc.). The image processing modules can generate images that can be optionally displayed at monitor 710 of the review and imaging system. Review and imaging system 700 may comprise controls that allow a reviewer to select and set parameter and settings for steps that take the additional data from the ultrasound machine to a final image.

Figure 8:
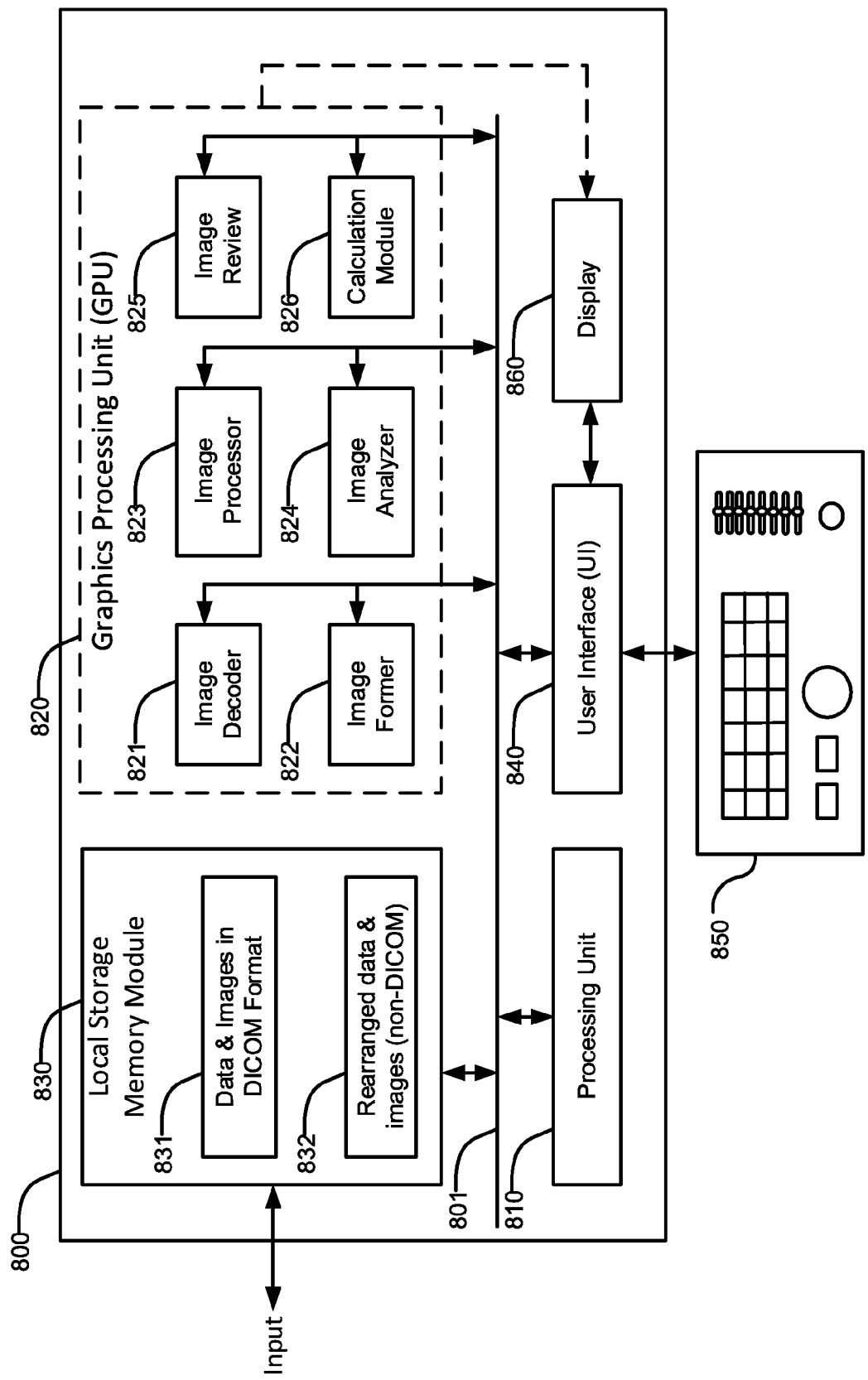
FIG. 8 is a block diagram of a review and imaging system according to an example embodiment.

FIG. 8 is a block diagram of a review and imaging system 800 according to an example embodiment. Review and imaging system 800 may comprise one or several modules. Review and imaging system 800 comprises a data and controls bus 801 that allows the transfer of data and controls between the various modules. Review and imaging system 800 comprises a processing unit 810 that coordinates the activities of the various modules. Processing unit 810 may be a central processing unit (CPU) having a process controller.

Review and imaging system 800 may further comprise one or several modules capable of processing images in some manner. These image processing modules may include, but are not limited to, image decoder module 821, image former module 822, image processor module 823, image analyzer module 824, image review module 825, and calculations, measurements and quantification module 826. The image processing modules may perform part of or all of an image processing chain that could be provided in an ultrasound machine.

In some embodiments, these image processing modules are implemented within a graphical processing unit (GPU) 820. Alternatively, the image processing modules may be implemented to operate on one or several hardware entities. For example, a module may be provided by a suitably configured data processor (configured by software and/or firmware), configurable logic circuit (such as a field-programmable gate array (FPGA), or custom logic circuits. Different modules may be provided by the same device or combination of devices or by different devices or combinations of devices. Thus, some modules may be implemented to operate on GPU 820 while some others may operate on processing unit 810 (e.g. CPU) or other logic circuits or devices. As a non-limiting example, the image review module 825 and the calculations, measurements and quantification module 825 may be implemented to operate on a CPU while the other image processing modules 821, 822, 823, and 824 may be implemented to operate on a GPU.

A user interface controller 850 providing an expanded range of controls may be used to interact with review and imaging system 800 through user interface 840. In some embodiments, user interface controller 850 may comprise an ultrasound keyboard. The ultrasound keyboard may be configured to control an image processing chain of review and imaging system 800 using controls of the same or similar types and functions as provided on an ultrasound machine.

Review and imaging system 800 may also include other modules (not shown) such as but not limited to a communications module that may support communication via wired or wireless data interfaces such as: USB, Bluetooth™, RS232, Ethernet, FireWire™ Thunderbolt™ interfaces. Review and imaging system 800 may comprise display 860. Display 860 may display the output of the image processing modules to a reviewer. In some embodiments, display 860 may communicate with and/or is a part of user interface 840.

Review and Imaging System: Local Storage Memory Module

Review and imaging system 800 may further comprise local storage memory module 830. Local storage memory module 830 may receive and store ultrasound images and additional data for review (e.g. from digital storage and archival system 70).

In some implementations local storage memory module 830 comprises a DICOM data storage section 831 and a non-DICOM storage section 832. When an exam is recalled by a reviewer operating a review and imaging system 800, data may be downloaded from an external storage (e.g. digital storage and archival system 70 in FIG. 1) to local storage memory module 830. The downloaded data may comprise parameters, settings, values and images, etc. The downloaded data may be in the DICOM format and temporarily stored in DICOM data storage section 831. In some embodiments, the downloaded data may be in non-DICOM format and directly stored in non-DICOM data storage section 832. An image decoder module 821 may read the downloaded data (DICOM or non-DICOM) and other information, decode the downloaded data, and store the decoded data and other information in non-DICOM data storage section 832.

Figure 9A:
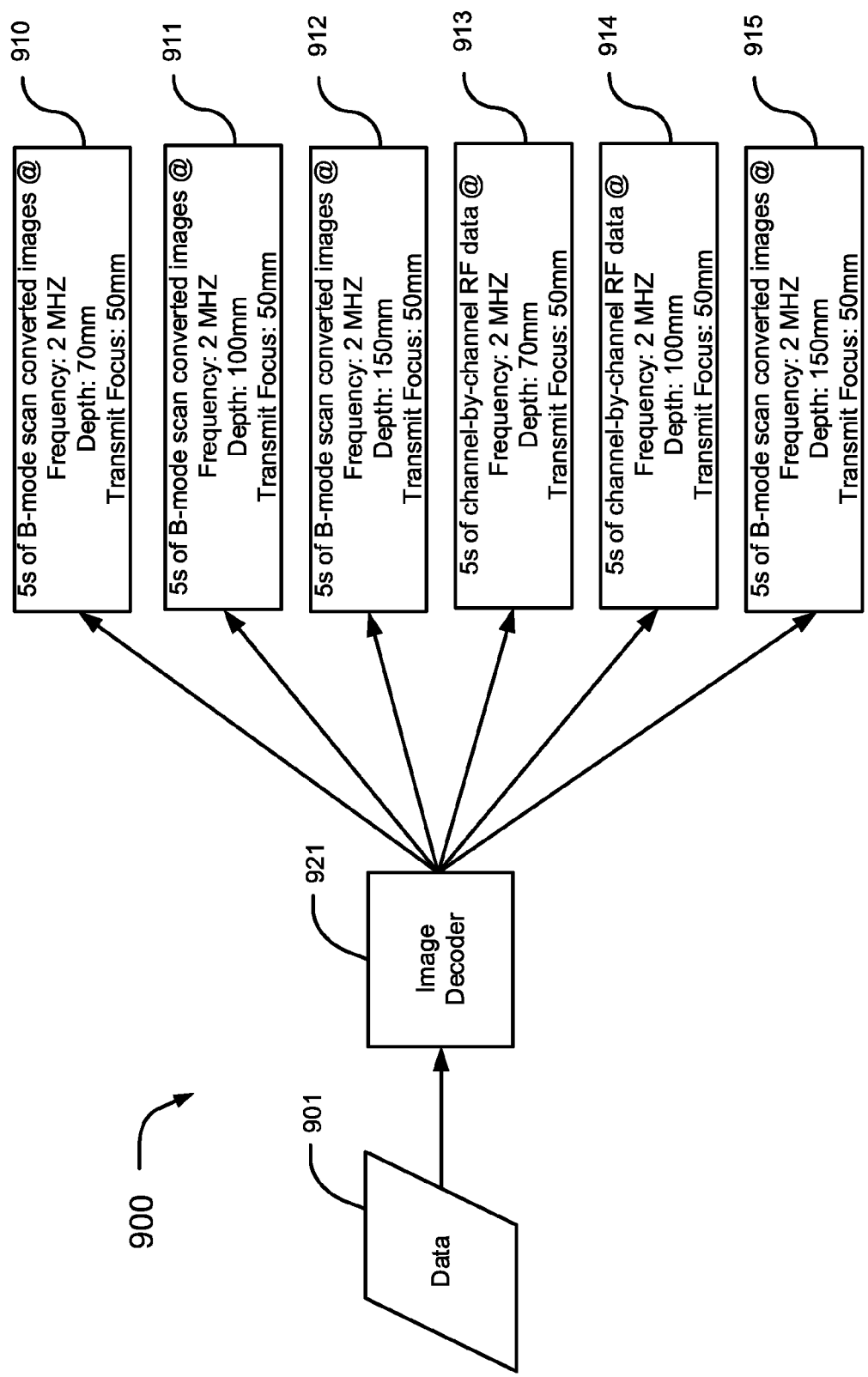
FIG. 9A is a block diagram illustrating a decoding operation within a review and imaging system according to an example embodiment of the invention.

FIG. 9A is a block diagram illustrating a decoding operation 900 within review and imaging system 800 according to an example embodiment of the invention. In this example, an ultrasound machine was instructed to collect both channel-by-channel RF data and scan converted data. Image decoder 921 (which may be a DICOM decoder if the DICOM format is used) decodes data 901 and separates data 901 into separate blocks as shown in boxes 910 through 915. These separate blocks of data can be placed in different segments of a memory module (e.g. local storage memory module 830). For example, the separate blocks of data can be stored non-DICOM data storage section 832. Further, other modules within review and imaging system 800 can access blocks 910 through 915 as appropriate.

In the example shown in FIG. 9A, blocks 910, 911 and 912 correspond to 5 s of scan converted images at an imaging frequency of 2 MHz, transmit focus of 70 mm, and an imaging depth of 70 mm, 100 mm and 150 mm respectively. With this data decoded and stored in local memory (e.g. local storage memory module 830), a reviewer may choose the imaging depth for an image to be displayed on display 860 through a user interface, such as a keyboard, and user interface controller 850.

In this example, blocks 913, 914 and 915 correspond to 5 s of channel-by-channel RF data at an imaging frequency of 2 MHz, transmit focus of 70 mm, and an imaging depth of 70 mm, 100 mm and 150 mm respectively. With this information, the reviewer can modify settings such as but not limited to apodization. In the specific case of apodization, the reviewer may, for example, choose between uniform apodization or Gaussian apodization to enhance the resolution of the image.

Local storage memory module 830 can store partial or complete results of computations or calculations that may be carried out by other modules in the review and imaging system (e.g. calculation module 826). Although local storage memory module 830 is illustrated as a separate block in FIG. 8, other configurations are possible. For example, memory may be distributed and may interface directly with other modules instead of to a central bus 801 as shown in the FIG. 8.

Figure 9B:
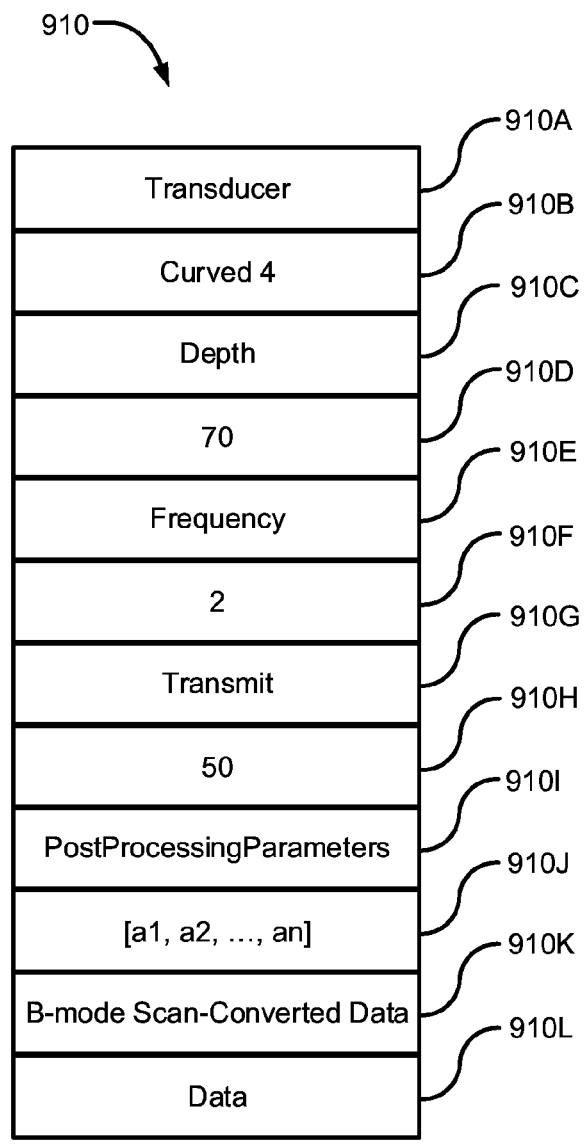
FIG. 9B is a schematic illustration of a memory organization that may be utilized during a decoding and encoding scheme for B-mode scan-converted data.

FIG. 9B is a schematic illustration of a memory organization that may be utilized during a decoding and encoding scheme for B-mode scan-converted data. In the example shown in FIG. 9B, the data organization within the review and imaging system 800 is similar to the data organization in an ultrasound machine.

FIG. 9B is an example of how information in block 910 can be stored in local storage and memory module 830. In FIG. 9B, memory location 910C stores the parameter "depth" while memory location 910D stores the value for this parameter. In this case, the value for the depth parameter is 70 (mm). Processing unit 810 can interpret the field in memory location 910C as the "depth" parameter and the field in 910D as the value of the "depth" parameter. After such interpretation, this value can be sent to the appropriate modules. This value may be used in multiple ways, including when image data contained in 910L are displayed on display 860 of review and imaging system 800. The information in memory location 910K informs review and imaging system 800 what type of data is contained in location 910L. Memory locations 910I and 910J provide one example of the type of image processing information that may be transferred from an ultrasound machine to the review and imaging system 800.

Memory location 9101 specifies that a post-processing parameter has been stored in memory location 910J. The post-processing parameters are sometimes referred to as the gray map. Thus the information in location 910J may be used when the images are displayed on review and imaging system 800. Using the post-processing parameters as an example, it may also be possible to save multiple settings for the same parameter. For example, in typical ultrasound machines, the user can choose between several post processing maps (gray maps). When data, parameters and other information are stored and captured within the ultrasound machine, all allowed values of the post-processing maps may also be stored. Thus when this information is decoded, there may be several pairs of memory locations that store data similar to the data stored in memory locations 9101 and 910K. With this information stored in local storage memory module 830 of review and imaging system 800, the reviewer may be able to have some or all of the same choices of post-processing parameters as if the user was using the ultrasound machine in a live imaging session. Thus, even if the user used a specific gray map during the live imaging session, the reviewer is able to choose the gray map that he or she prefers during review of the images on review and imaging system 800.

The example of the post-processing parameters illustrates the concept that review and imaging system 800 is able to accept data from one or multiple types of ultrasound machine (including different brands and models), and provide controls to the reviewer similar to what may be available to him or her on an ultrasound machine. For example, ultrasound machine A may only allow two different post-processing parameter sets whereas ultrasound machine B may allow five different post-processing parameter sets. When the data is decoded by review and imaging system 800, there may be only two pairs of memory locations similar to 9101 and 910J for ultrasound machine A, whereas there may be five pairs of memory locations similar to 9101 and 910J for ultrasound machine B. In another example, review and imaging system 800 may provide post-processing options that go beyond those available on an ultrasound machine used to acquire an image. For example review and imaging system 800 may provide more than two pairs of memory locations similar to 9101 and 910J for ultrasound machine A.

Figure 9C:
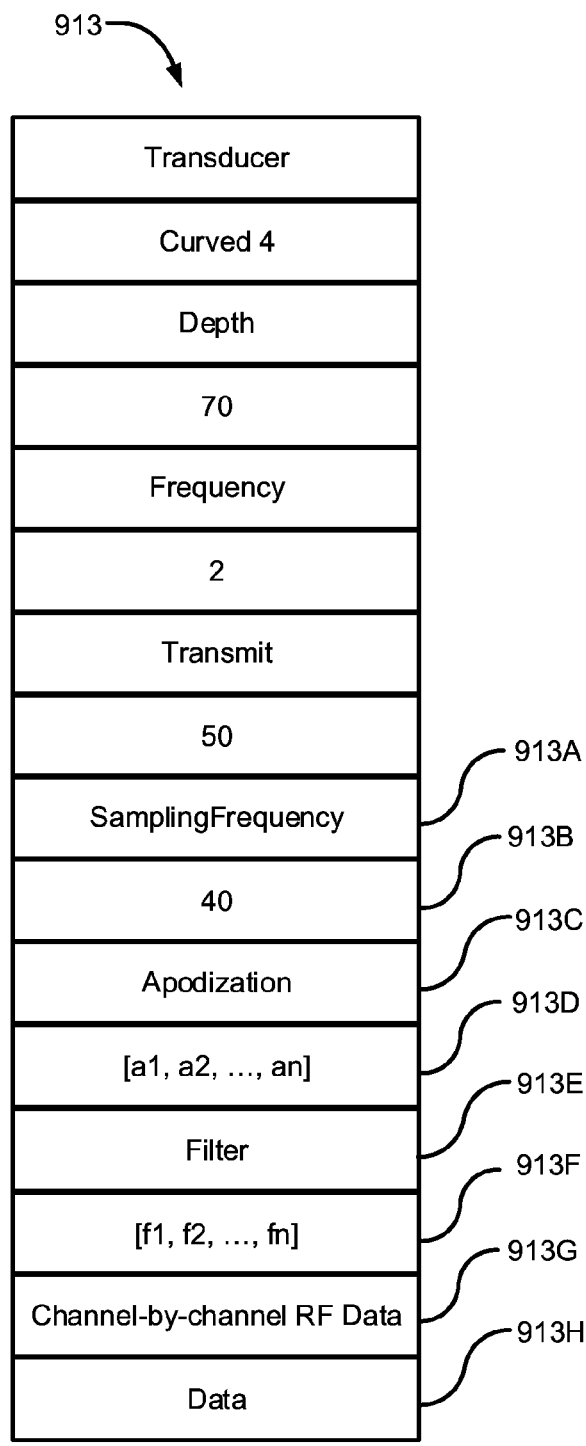
FIG. 9C is a schematic illustration of a memory organization that may be utilized during a decoding and encoding scheme for channel by channel RF data.

FIG. 9C is a schematic illustration of an example memory organization that may be utilized within review and imaging system 800 for channel-by-channel RF data indicated in block 913. Information in block 913 may be different from information in block 910. For example, memory location 913A stores the parameter "sampling frequency" while memory location 913B stores the value of this parameter. Memory locations 913C to 913E will be discussed in the subsequent section.

Review and Imaging System: Image Former

Image former 822 may be implemented on various computational resources such as but not limited to a digital signal processor (DSP), a graphics processing unit (GPU), a central processing unit (CPU), an FPGA, custom logic circuits or any combination of two or more of these. FIG. 8 illustrates an implementation on a GPU. In some embodiments, the computation that is performed within the image-former depends in part on the type of data that is input.

Eqn. 1 below illustrates the concepts above with one example computation that may be carried out within image former 822. In this example, the transducer of an ultrasound machine has N elements and a synthetic aperture type of imaging is performed on the ultrasound imaging system. In this specific example, one transducer element at a time is used to transmit energy followed by reception of echoes of that energy. Each echo signal is received at one transducer element. In an example case, the ultrasound machine performs $N^2$ firings to achieve transmit from every element and receive on every element (one at a time). With this understanding, each pixel on an image plane can be formed by:

$$P(x, y) = \sum_{tx=1}^{N} \sum_{rx=1}^{N} A_{tx,rx}(x, y) f_{tx,rx}(x, y) S_{tx,rx}(x, y) \quad [\text{Eqn. 1}]$$

Here x, y are coordinates within an image plane. The image plane may have a one-one correspondence to the display plane (or display screen) but other relationships are not excluded. Also:

$A_{tx,rx}(x, y)$ is the apodization function where this function can be dependent on the specific transmit element tx and specific receive element rx that are being considered for making an image at x,y;

$f_{tx,rx}(x, y)$ is a filter function. The filter function can be dependent on the specific transmit element tx and specific receive element rx that are being considered for making an image at x,y and $S_{tx,rx}(x, y)$ is the signal at x,y when the transmit element tx is fired and receive element rx is used to receive this energy.

For the parameters above, it is assumed that the transducer location is known and is in the same plane that contains the pixel locations x,y.

Relating this example to the decoded information illustrated in FIG. 9C, $S_{tx,rx}$ may be the RF channel-by-channel data stored in memory location 913H, $A_{tx,rx}$ may be the apodization values stored in memory location 913D and $f_{tx,rx}$ may be the filter coefficients stored in memory location 931F. Thus with the specific organization illustrated in FIG. 9C, review and imaging system 800 may use Eqn. 1 to generate images using the RF data stored in memory location 913H and parameters stored in other memory locations.

Figure 9D:
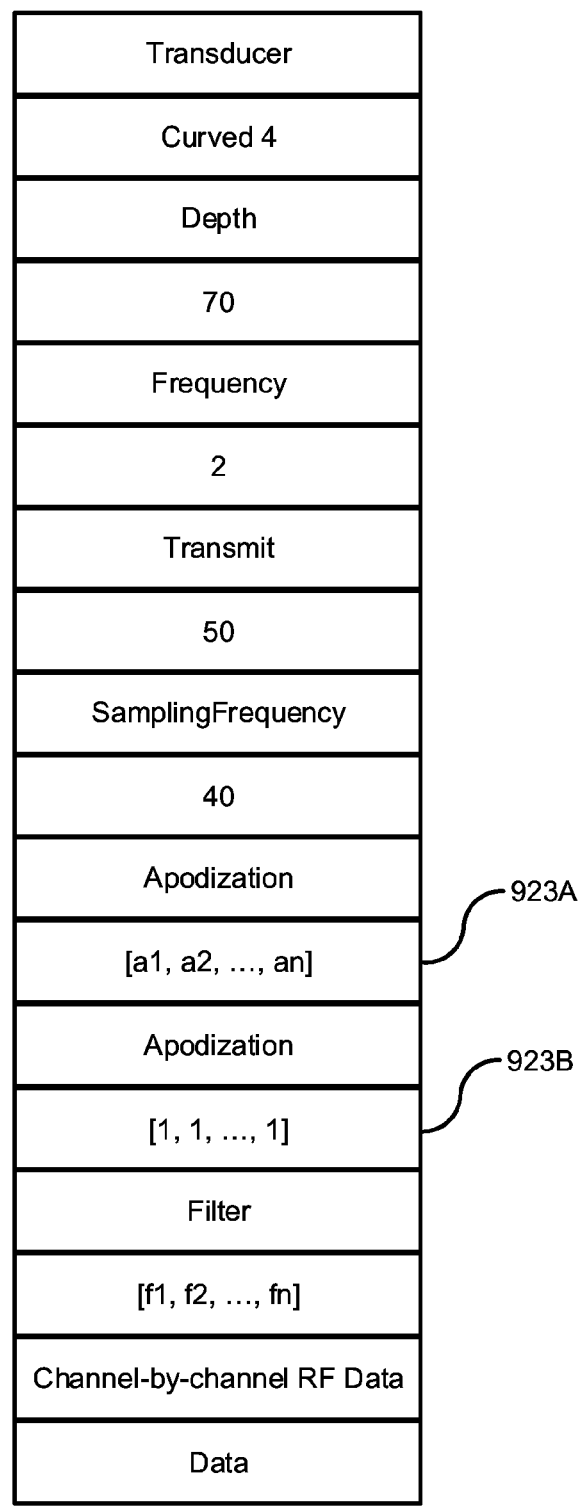
FIG. 9D is a schematic illustration of a memory organization that may be utilized during a decoding and encoding scheme for channel by channel RF data having multiple values for a parameter.

FIG. 9D is a schematic illustration of a memory organization that may be utilized during a decoding and encoding scheme for channel-by-channel RF data having multiple values for a parameter according to an example embodiment. Here, two sets of apodization values are stored (from the ultrasound machine) and available for review and imaging system 800 after decoding. The two sets of apodization values are stored in memory locations 923A and 923B. The coefficients $a_1$ through $a_n$ may be specified to apply a Hamming apodization. The coefficients in memory location 923B are all 1 s, indicating uniform apodization if the values in memory location 923B are utilized. In the example demonstrated in FIG. 9D, a reviewer has a choice between two apodization functions—he or she can choose the Hamming apodization if less side lobe noise is preferred, or uniform apodization if high resolution is preferred. Thus, the reviewer has the flexibility to change parameters that are normally adjusted on ultrasound machines on review and imaging system 800. These parameters may affect image quality.

In general, review and imaging system 800 is capable of accepting data from any type of ultrasound machine and generating images based on the data. In some embodiments, each ultrasound machine may utilize its own filtering functions, apodization functions, and/or other signal processing and image processing functions. When the data, parameters and other information are captured, each ultrasound machine may store its specific information. This information is transferred to the review and imaging system 800 and the specific information pertaining to the ultrasound machine may then be utilized to generate images. These images would therefore be the same or similar to the images generated on an ultrasound machine.

In the example above, although computations such as application of apodization were determined by the data, parameters and other information captured and stored on the ultrasound machine, review and imaging system 800 may optionally in addition or in the alternative perform other computations and/or other processing to generate images. Consider the example of an ultrasound machine that only uses Hamming apodization for receive side processing. If channel-by-channel RF data were to be captured from this example ultrasound machine, review and imaging system 800 may provide the capability of also applying uniform apodization or other apodization functions.

This functionality may be achieved in any of several ways. In one way, a table may be programmed within the review and imaging system that specifies various computations that may be performed to each data type. Thus, for the example of channel-by-channel RF data, the table may specify allowed computations that may include without limitation pixel summation, apodization, and/or filtering. Further, in the example of apodization, review and imaging system 800 can specify multiple sets of n coefficients, where each set corresponds to a specific apodization. In some embodiments, the reviewer adjusts the apodization through user interface 840.

Figure 10:
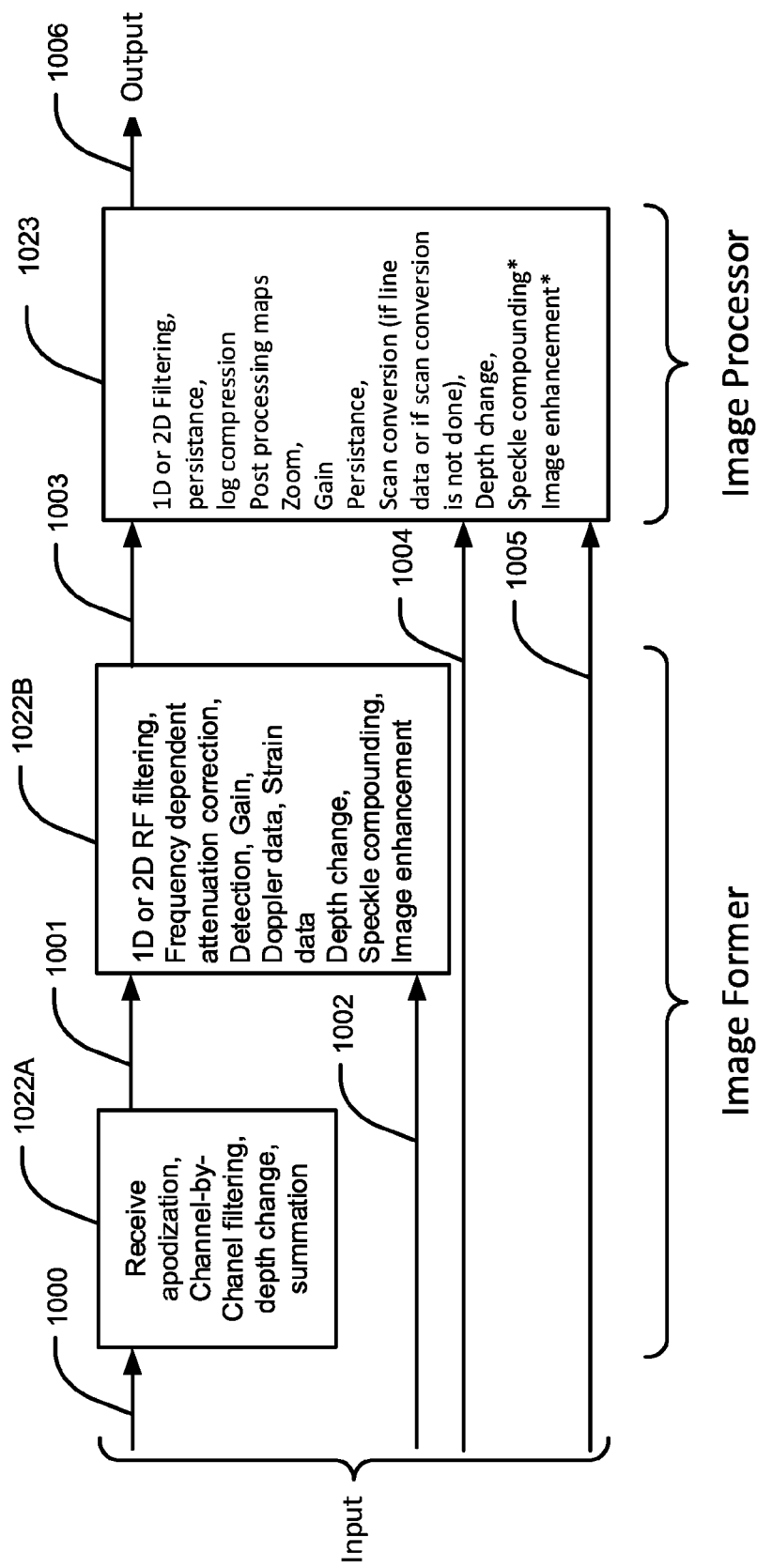
FIG. 10 is a functional flow diagram showing a signal processing chain in a review and imaging system according to an example embodiment.

FIG. 10 is a functional flow diagram showing a signal processing chain for a review and imaging system 800 according to an example embodiment. Processes 1022A and 1022B illustrate the type of computations that can be performed with different types of data available to image former 822. Input data 1000, 1002, 1004 and 1005 from different stages in an image processing chain of an ultrasound machine enters the signal processing chain at different points.

In process 1022A, channel-by-channel receive RF data 1000 is input into image former 822. This type of data may be available if a synthetic aperture type of imaging format was utilized during the live imaging session by the ultrasound machine. Process 1022A provides a few examples of computations that can be performed with this data. This list includes but is not limited to application of receive apodization, application of filters on a channel-by-channel basis, application of gain on a channel by channel basis, summation of RF data for a particular pixel location, etc.

Some embodiments provide the ability to change the gain on a line-by-line or channel-by-channel basis on a review and imaging system. This feature can allow different reviewers to choose different gain settings to examine different regions in more optimal ways. For example, the gain near the side of an image may be boosted without adjusting the gain near the middle of the image. This may prevent the middle of the image from becoming a distraction.

The output of process 1022A may include pixel data or line-by-line data 1001. Line-by-line output 1001 may be configured to simulate acoustic lines, with each line associated with a steer direction relative to the transducer that was used to obtain the data. Thus for a line-by-line output 1001, x,y coordinates may be calculated along a simulated line or a steer direction with the computations for Eqn. 1 performed along these coordinates.

If the ultrasound machine is configured to store and transfer RF line-by-line data 1002 (rather than channel-by-channel data 1000), RF line-by-line data 1002 can be transferred as input to process 1022B. In this block, some example computations that can be carried out include but are not limited to 1D or 2D filtering, correction for frequency dependent attenuation, adjustment of gain, other RF based processing such Hilbert transformation and detection, etc. The output of process 1022B may include detected pixel data or line or detected line-by-line data 1003. The output of process 1022B may also include results of other processing such as but not limited to Doppler processing and strain processing. The processing steps and the order of processing within process 1022B may be determined by the data, parameters and other information stored on the ultrasound machine.

Review and imaging system 800 may also provide additional capabilities that were not available on the ultrasound machine used to obtain the ultrasound image data and additional data. With these capabilities, data from one or multiple types of ultrasound machines may be processed within review and imaging system 800.

Eqn. 2 provides an example of a computation that may occur in process 1022B within image former 822 when the input is line-by-line data 1001 or 1002. Line-by-line data 1002 can be created by the ultrasound machine, or as explained above, line-by-line data 1001 can be created by process 1022A of image former 822. When the ultrasound machine is creating the line-by-line data, one acoustic frame may be created with multiple lines that correspond to multiple steer directions. For reference, in a typical imaging sequence using sum-delay-beamforming, a transducer fires a number of transmissions and forms another number of receive lines for each transmission. Each of these lines corresponds to a steer direction. The set of lines that make up an acoustic frame is chosen to cover a desired spatial or angular extent of the object being scanned.

An example computation that can be performed in process 1022B is to convert line-by-line data 1001 and/or 1002 to detected line-by-line data 1003. During this process of detection, other operations can be performed upon the RF line such as but not limited to applying depth dependent gain or applying filters such as a filter to correct for frequency dependent attenuation. Eqn. 2 provides an example for this process of detection.

$$B_m(d) = |g_m(d)v_m(d)RF_m(d)|^2 \qquad [\text{Eqn. 2}]$$

Here:
  m refers to the $m^{th}$ line;
  d refers to the depth (or distance from the transducer);
  $g_m(d)$ refers to the depth dependent gain for the $m^{th}$ line;
  $v_m(d)$ refers to a function that accommodates or corrects for depth dependent attenuation for the $m^{th}$ line;
  $RF_m(d)$ refers to the $m^{th}$ input RF line;
  $B_m(d)$ refers to the $m^{th}$ output detected line; and
  symbol | ... | refers to the detection process (or taking the magnitude of the RF line).

Given an RF line-by-line input in example Eqn. 2, a reviewer can choose various values of gain. Each ultrasound machine typically has its own gain curve that may be stored and transferred to the review and imaging system. The reviewer may choose the gain curve utilized by the ultrasound machine from where the data originated or use a curve that may be provided by the review and imaging system.

Review and imaging station 800 may give a reviewer a choice of how to accommodate frequency dependent attenuation. In this situation, the reviewer may choose a curve that was utilized by the ultrasound machine or use a curve provided by the review and imaging system.

The ability to change the gain of the RF signal on a line-by-line basis provides the advantage that the gain of the lines in the edges of the image may be adjusted to be higher than those at the center. Typically, the lines at the edges suffer from poorer signal-to-noise ratio so having the ability to change the gain of the edge lines helps achieve uniformity within the image. Image uniformity may contribute to better diagnosis and may be beneficial to a patient.

As previously discussed, the computations performed within image former 822 may depend on the type of data that is input. Thus, process 1022B in FIG. 10 can receive either pixel data or line-by-line data 1001. Eqn. 2 illustrates an example computation that can be performed in block 1022B if line-by-line data is the input. Eqn. 3 illustrates an example computation that can be performed in block 1022B in the process of detection when pixel data is the input.

$$B(x,y)=|g(x,y)v(x,y)RF(x,y)|^2 \qquad \text{[Eqn. 3]}$$

Here:
 B(x, y) is the output detected pixel brightness data at a coordinate defined by x, y;
 RF(x,y) is the input RF pixel data at a coordinate defined by x, y;
 g(x, y) is the gain that is applied to the input RF pixel data RF(x,y) as a function of x,y;
 v(x, y) is a function that accommodates or corrects for depth dependent attenuation as a function of x,y; and
 symbol | . . . | refers to the detection process (or taking the magnitude of the RF data).

The above computation can be performed for all valid ranges of x and y. The ranges may be predefined.

Thus, Eqn. 2 and Eqn. 3 illustrate how different computations may be performed in process 1022B of image former 822 depending on the input data. In these examples, the same result is obtained (that of detection), but the details of the computations are different.

Although FIG. 10 shows the functions of the image former split into two boxes, the functions may be combined into one computation engine in other configurations. In particular, the computations may be accomplished by one set of hardware or firmware.

Review and Imaging System: Image Processor

The output of process 1022B of image former 822 may be the input to process 1023 of image processor 823. The input to the process 1023 may include detected pixel or line-by-line data 1003 from the image former 822, or scan-converted data 1004 or detected line-by-line data 1005 generated by the ultrasound machines. As in image former 822, the computations that may be performed by image processor 823 depend in part on the type of input. If detected pixel or line-by-line data 1003 is the input, example computations that may be performed include but are not limited to one or a combination of 1 D-2D filtering, zoom, gain, etc.

If the input to image processor 823 is detected pixel data, then the following example computation may be performed. Assuming $P_{in}(x, y)$ is the input detected pixel brightness data at (x, y) then, $$P_{out}(x,y)=T_B(20*\log_{10}(g_d(x,y)*P_{in}(x,y))) \qquad \text{[Eqn. 4]}$$

where:
 $P_{out}(x, y)$ is the output pixel brightness data at (x,y);
 $g_d(x,y)$ is the two dimensional gain that can be applied to an input detected pixel;
 $\log_{10}(g_d(x,y)*P_{in}(x, y))$ is the logarithm of a gained input function; and
 $T_B$ is the process of applying a post-processing map that maps an input brightness to an output brightness.

Gain values may be: obtained from the ultrasound machine generated data or generated in the review and imaging system. In Eqn. 4, three computations are applied: applying a two dimensional gain to the input brightness pixel, taking the log of the product, and applying a post-processing map.

If the input to image processor 823 is line-by-line detected data, then the following example computation may be performed. This example illustrates a similar process of applying a gain and computing the log of the detected data followed by application of a post-processing curve and a process of scan conversion. Thus if $P_{det}'(d)$ is the $d^{th}$ sample of the line-by-line input detected data then:

$$P_{det}''(m,n)=20*\log_{10}(g(m,n)*P_{det}'(m,n)) \qquad \text{[Eqn. 5A]}$$

Where:
 m is the $m^{th}$ sample and n is the $n^{th}$ line;
 $P_{det}''(m,n)$ is the gained, logged input $P_{det}'(m,n)$ ($m^{th}$ sample of the $n^{th}$ line); and
 g(m,n) is the gain applied to the $m^{th}$ sample, $n^{th}$ line.

Next, assuming that $P_{det}''(m,n)$, $P_{det}''(m, n+1)$, $P_{det}''(m+1, n)$, $P_{det}''(m+1, n+1)$ are the four nearest samples (in length units) to a output pixel x,y where m stands for a line m and n stands for the nth sample in that line, then the process of scan conversion can be depicted as:

$$G(x,y)=T_B(S(P_{det}''(m,n),P_{det}''(m,n+1),P_{det}''(m+1,n), P_{det}''(m+1,n+1))) \qquad \text{[Eqn. 5B]}$$

Here:
 G(x,y) is the output scan converted value at (x,y);
 $(S(P_{det}''(m,n), P_{det}''(m, n+1), P_{det}''(m+1, n), P_{det}''(m+1, n+1)))$ represents the scan conversion function that is typically a bilinear interpolation between the four samples P(m,n), P(m, n+1), P(m+1, n), P(m+1, n+1); and
 $T_B$ is the post-processing function as defined in Eqn. 4.

While the scan conversion algorithm described above uses the nearest four neighbors and bilinear interpolation, other scan conversion algorithms may also be used. Such algorithms may be different from or the same as those utilized by the ultrasound machine that was used to capture the data. Details of the scan conversion algorithm the ultrasound machine is using may be stored and transferred to review and imaging system 800.

Figure 11:
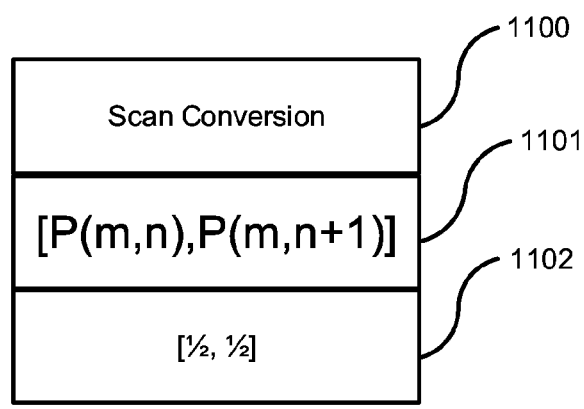
FIG. 11 is schematic illustration of how details of an algorithm may be stored and transferred between an ultrasound machine and a review and imaging system.

FIG. 11 is schematic illustration of how details of an algorithm may be stored and transferred between an ultrasound machine and a review and imaging system. In this example, it is assumed that the scan conversion algorithm uses only two nearest neighbors and the computation itself is taking the mean of the two nearest neighbors. As part of the capture and store process, the ultrasound machine may use a structure same as or similar to the ones outlined in FIGS. 9B and 9C for storing the names of and the details of the algorithm. Memory location 1100 indicates the name of the algorithm, memory location 1101 instructs review and imaging system 800 to use the two nearest neighbors, and memory location 1102 instructs the review and imaging system to add half of each of these two nearest neighbors. The private data encoder on the ultrasound machine and the private data decoder on the review and imaging system work in tandem to code and decode information. Once the information is decoded, the processing unit 810 sends the instructions and data to the appropriate modules within review and imaging system 800.

If the input to image processor 823 is scan converted data, then the following example computation may be performed.

$$R(x,y) = T_B(Q(x,y)) \quad [\text{Eqn. 6}]$$

Here:
 Q(x,y) is the input scan converted data;
 R(x,y) is the output value at (x,y); and
 $T_B$ is the postprocessing function as defined in Eqn. 4.

Depending on the type of data that is stored on the ultrasound system and eventually transferred into review and imaging system 800, different types of computations may be performed on review and imaging system 800. In one example, the reviewer is able to change the depth while performing the review. Functions such as depth change can be implemented if they are supported by the appropriate data. To support the depth change at review and imaging system 800, sufficient amount of data from the appropriate receive channels in the ultrasound machine should be captured, digitized and transferred to review and imaging system 800.

In addition to process 1022A, if channel-by-channel data is stored and transferred to review and imaging system 800, then processes 1022B and 1023 may also be recruited to perform additional computations. The equations below illustrate this concept. For example, consider the following equation:

$$I_{RF} = \sum_{x=0}^{L_d} \sum_{y=0}^{D} P(x, y) \quad [\text{Eqn. 7}]$$

where:
 $I_{RF}$ is the set of RF pixels computed by process 1022A;
 P(x,y) is as computed in Eqn. 1;
 D is the imaging depth that is chosen by the reviewer; and
 $L_d$ is the spatial extent in x direction.

In a linear transducer, the x-direction is the direction along the length of the transducer and the y-direction (depth direction) is the direction perpendicular to the x-direction. In a curved transducer, the x direction is parallel to the chord that connects the ends of the curve that defines the transducer face and the y-direction is perpendicular to the x-direction. The subscript d associated with the parameter L indicates that the extent of the computations along the x-direction varies with the distance of the computed pixel located at (x,y) from the transducer face. In a linear transducer, where the image typically has a rectangular format, there is typically no variation in $L_d$ as a function of depth. However in a curved transducer where the image typically has a format that resembles a hand held fan (fan beam), for each depth, the extent over which the computations have to be done varies. These nuances are well known and widely utilized.

Returning back to the concept of how imaging depth change is implemented within block 1022A, eqn. 7 states that P(x, y) is computed over the appropriate ranges of x and y to support the imaging depth D chosen by the reviewer.

Next, block 1022B can perform depth dependent computations over the chosen depth. Thus if $I_{det}$ is the set of all detected pixels computed by box 1022B, then $$I_{det} = \sum_{x=0}^{L_d} \sum_{y=0}^{D} B(x, y) \quad [\text{Eqn. 8}]$$

where:
 B(x,y) is computed by eqn. 3;
 D is the imaging depth that is chosen by the reviewer; and
 $L_d$ is the spatial extent in x direction.

This equation states that B(x, y) is computed over the appropriate ranges of x and y to support the imaging depth D chosen by the reviewer.

Similarly, process 1023 may also support an imaging depth change. Here, if $I_{final}$ is the set of all (imaging related) pixels that are finally displayed on a screen, then, $$I_{final} = \sum_{x=0}^{L_d} \sum_{y=0}^{D} P_{out}(x, y) \quad [\text{Eqn. 9}]$$

where:
 $P_{out}(x, y)$ is computed by eqn. 4;
 D is the imaging depth that is chosen by the reviewer; and
 $L_d$ is the spatial extent in x direction.

If channel-by-channel RF data 1000 is stored and transferred to review and imaging system 800, it can be seen in FIG. 10 that blocks 822A, 822B and 825 may all be applied to perform the computations. If line-by-line RF data 1002 is being stored and transferred to review and imaging system 800, blocks 822B and 825 may be the only processes required to perform the computations. The equations below illustrate the computations for this example. In this example, if $I_{line,det}$ is the set of all detected lines computed by block 1022B, then:

$$I_{line,det} = \sum_{m=1}^{M} \sum_{d=0}^{D} B_m(d) \quad [\text{Eqn. 10}]$$

where:
 $B_m(d)$ is calculated according to Eqn. 2;
 m is the mth line and can assume values between 1 and M;
 d is the depth or distance from the transducer and can assume values between 0 and D; and
 D is the imaging depth chosen by the reviewer.

Following the computation of Eqn. 10, scan conversion can be carried out by computing Eqn. 5B over the appropriate ranges of x and y.

If scan-converted data 1004 is being stored and transferred to review and imaging system 800, then process 1023 is performed. In this case, the ultrasound machine should be set up to capture scan converted data at multiple imaging depths. Image processor 823 selects the images corresponding to the depth that the reviewer has selected. For example, image processor 823 may select the data from block 910, 911, or 912 in FIG. 9A.

Functions such as but not limited to depth change, image enhancement and speckle compounding may be supported by one or multiple blocks in FIG. 10, depending on the data that is being stored at the ultrasound machine and transferred. For speckle compounding, various methods exist such as but not limited to spatial compounding and frequency compounding. For the frequency compounding example, if line-by-line RF data is being stored and transferred, then process 1022B may perform operations on each different type of line. The frequency dependent attenuation correction filters, for example, may be different for the lines that are acquired with different center frequencies of transmission. In this case, process 1022B may output detected lines after performing different calculations. The summation of these lines may occur in process 1023. On the other hand, if scan converted data was being captured and stored in the ultrasound machine and transferred, scan converted images formed on the ultrasound machine with different frequency content of the underlying RF signals may be input directly into process 1022B where they can be summed (unless the summing already was accomplished on the ultrasound machine).

In another example, some functions such as but not limited to log compression can be accomplished by process 1023 alone. Other functions in this category include zoom and post-processing maps.

The output 1006 of process 1023 may be sent for display. The reviewer may also have the option of storing the results for future reference. The results may be stored locally or may be transferred back to a digital image storage and archival system (e.g. archival system 70 in FIG. 1).

It is to be generally understood that for one or all the various processing steps described above, the specifications of the processing may be provided in multiple ways including but not limited to being provided by the ultrasound machine through the encoding and decoding schemes described earlier. The specification may also be provided by the review and imaging system. Thus with this type of capability, the review and imaging system may generate images that the ultrasound machines itself generate. However, by using its own native capabilities, the review and imaging system may also generate images that cannot be generated on the ultrasound machines.

Review and Imaging System: Image Analyzer

Review and imaging system 800 may also include image analyzer 824 as shown in FIG. 8. Image analyzer 824 may be another computation engine that performs various functions such as but not limited to obtaining image based statistics including mean, standard deviation, moment, etc., classifying images or regions within images according to some preset criteria, produce results based on machine learning algorithms, perform fusion of ultrasound images with images from other modalities, and perform measurements and calculations. Image analyzer 824 may be configured to accept different types of data, including but not limited to data from image former 822 or image processor 823.

A few examples of the types of computations that can be performed by image analyzer 824 are demonstrated below. In the first example, the ratio of the mean to the standard deviation of a region within an image can be calculated, for example by the following formula:

$$\mu = \frac{1}{N}\sum_{1}^{N} A_n \qquad \text{[Eqn. 11]}$$

Where:
  $\mu$ is the mean of a patch of an ultrasound image consisting of N samples; and
  $A_n$ is the amplitude of the envelope of RF signal at the $n^{th}$ sample.

Along with the mean, the standard deviation for the same patch may be calculated as follows:

$$\sigma = \frac{1}{N}\sum_{1}^{N}(A_n - \mu)^2 \qquad \text{[Eqn. 12]}$$

Where:
  $\sigma$ is the standard deviation;
  $\mu$ is the mean of a patch of an ultrasound image;
  N is the number of samples; and
  $A_n$ is the amplitude of the envelope of RF signal at the $n^{th}$ sample.

Here the patch of the image that is included within the calculation can be drawn as appropriate. Ways to establish the boundary of the patch include, but are not limited to, manual, automatic or a combination of manual and automatic. Automatic methods include but are not limited to methods based on edge detection and methods based on machine learning and classification. For example, the brightness (e.g. amplitude squared) of a particular sample along with the sample's proximity to another bright sample may be used to include this sample in the calculation.

The following ratio may be found for this patch:

$$k = \frac{\mu}{\sigma} \qquad \text{[Eqn. 13]}$$

where:
  $\sigma$ is the standard deviation;
  $\mu$ is the mean of a patch of an ultrasound image;

For an area containing "pure speckle" this ratio is known in the art to be approximately equal to 1.91. Pure speckle is defined by a region that has a large number of randomly distributed scatterers within the resolution cell of the ultrasound machine.

There are a number of ways of utilizing ratio k. For example, ratio k may be found for multiple areas within an organ such as a liver. By doing so, areas with ratios that are different than areas with similar ratios may be found. If the ratios are different by more than a threshold value, such areas may be flagged. The flagging operation may then alert the reviewer to pay attention to such areas. The multiple areas within the liver (or other organ or tissue) may be defined by the reviewer manually. Alternatively, automatic techniques may also be utilized.

In another example, ratio k may be found for multiple areas within the liver or other organs for multiple patients. The reviewer can classify the areas in one of several ways such as diseased or non-diseased. Within the diseased classification, the reviewer can further classify the areas according to the type of disease.

In yet another example, ratio k for one patient may be compared against a population ratio. The population ratio may be calculated 'locally' by image analyzer 824 using the images of the patients reviewed at a review and imaging system or it may be obtained from an external source such as an external database. If the ratio is calculated locally, the population may include multiple subsets such as but not limited to all patients imaged on all brands of ultrasound machines at that specific imaging center or patients imaged on one specific brand of ultrasound machine by a specific user. The reviewer may define inclusion criteria in the computer programs within the review and imaging system such that the appropriate patients are included. To accomplish this, a search engine that looks through the patient records may be provided within the review and imaging system. The patient records may be accessible through interaction with the electronic medical record system.

The examples above only illustrate certain types of computation, and other computations are not excluded. In addition, while the example above describes the liver, the discussion applies to other organs as well.

Review and Imaging System: User Interface

Commercial ultrasound machines typically have a specialized user interface. As seen in FIG. 7, review and imaging system 700 may be interfaced to an ultrasound keyboard (e.g. ultrasound keyboard 730). Since ultrasound machines from different manufacturers may be used in different settings, a review and imaging system may comprise a generalized ultrasound keyboard instead of a customized ultrasound keyboard from a single manufacturer. The layout of a generalized ultrasound keyboard on a review and imaging system may be different from the layout of an ultrasound keyboard on the ultrasound machine used to acquire the data. The various functions found on an ultrasound keyboard on an ultrasound machine may be mapped to keys or knobs or other types of actuators on the generalized ultrasound keyboard.

Figure 12A:
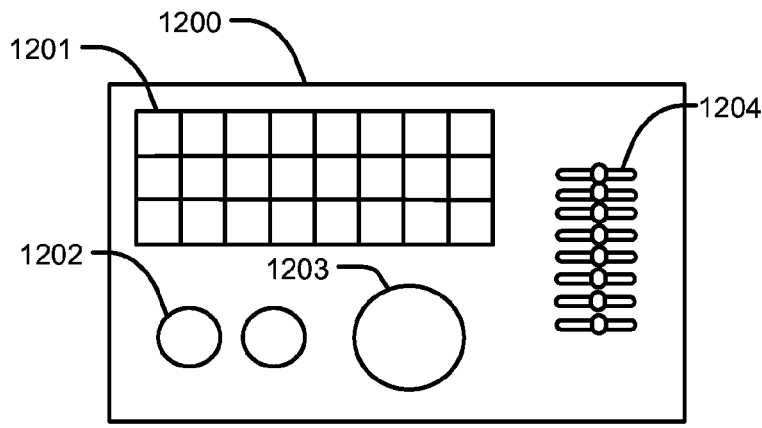
FIGS. 12A and 12B illustrate examples of ultrasound keyboards found on conventional ultrasound machines.
Figure 12B:
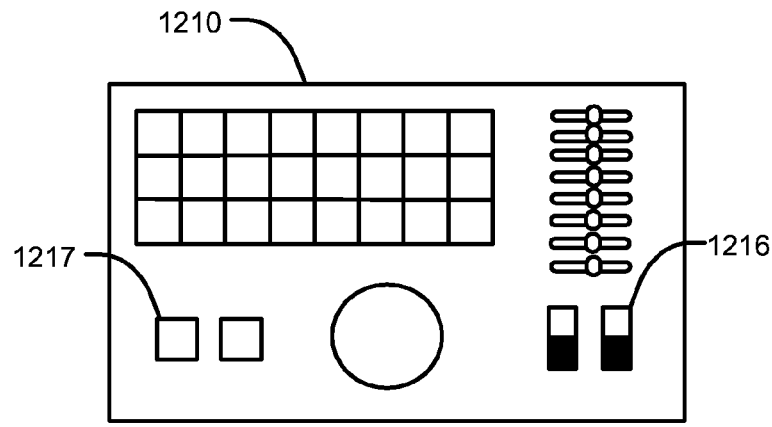

FIGS. 12A and 12B illustrate examples of ultrasound keyboard configurations that may be found on conventional ultrasound machines. In the example shown in FIG. 12A, ultrasound keyboard 1200 comprises keypad 1201, control knobs 1202, trackball 1203 and sliders 1204. In the example shown in FIG. 12B, ultrasound keyboard 1210 comprises toggle switches 1216 and push buttons 1217, but does not have any control knobs. Ultrasound keyboards 1200 and 1210 may be configured differently such that the same function (e.g. imaging depth control, brightness, etc.) is provided by different controls for different ultrasound machines.

Figure 12C:
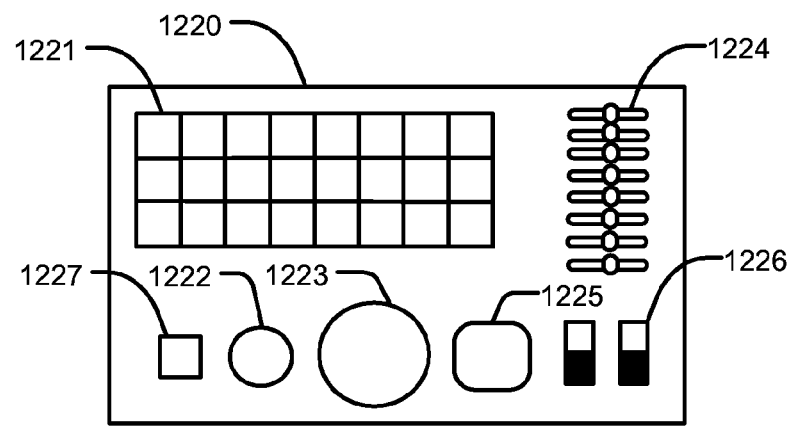
FIG. 12C illustrates one example configuration of an ultrasound keyboard that may be interfaced with a review and imaging system.

FIG. 12C illustrates one example configuration of generalized ultrasound keyboard 1220 that may be interfaced with a review and imaging system. As seen in FIG. 12C, generalized ultrasound keyboard 1220 may be designed to have an overabundance of control inputs so that the controls found on even the most complex ultrasound keyboard of commercial ultrasound machines may be mapped to an individual control of generalized ultrasound keyboard 1220. An overabundance of control inputs also allow functions found in different locations in keyboards interfaced to ultrasound machines from different manufacturers to be mapped to a similar control input on generalized ultrasound keyboard 1220.

In the example embodiment shown in FIG. 12C, ultrasound keyboard 1220 comprises keypad 1221, control knobs 1222, trackball 1223, sliders 1224, pointing device 1225, toggle switches 1226, and push buttons 1227. This kind of configuration has the advantage that regardless of the ultrasound machine utilized for acquiring the data, the reviewer may interact with the data acquired from the different ultrasound machines in the same way. For example, imaging depth control may be implemented though control knob 1202 on the left side of ultrasound keyboard 1200, and through toggle switches 1216 on the right side of ultrasound keyboard 1210. Regardless of these differences, the imaging depth control maybe mapped to the same control (e.g. knob, button, sliders, etc.) located at a convenient location on generalized ultrasound keyboard 1220 (e.g. knob 1222).

Referring back to FIG. 8, user interface control 850 may comprise a generalized ultrasound keyboard (e.g. generalized ultrasound keyboard 1220). In these circumstances, the mapping function may reside either within processing unit 810 or within a module in GPU 820. When the data, parameters and other information are captured and stored on an ultrasound machine, one body of information that may be stored may include information that specifies the controls provided on that ultrasound machine and its keyboard. This information can be transferred to review and imaging system 800. The mapping function within review and imaging system 800 may assign these controls to various locations on the generalized ultrasound keyboard. To do so, the mapping function may store the mapping information in the form of a table or other mechanisms where various controls exist on the generalized ultrasound keyboard.

Although the example above describes the concept for the imaging depth function, this concept may be utilized for other functions that are commonly found in most ultrasound machines. Functions that are specific to an ultrasound machine may also be mapped to certain control inputs on a generalized ultrasound keyboard. The mapping may be displayed on the display screen of a review and imaging system, or indicated in some other manner such as but not limited to displaying the mapping with miniature liquid crystal displays that may be located adjacent to the control inputs on a generalized ultrasound keyboard.

In another example embodiment, a user interface device is provided and includes functions that are most frequently used and commonly found on almost all ultrasound machines such as but not limited to overall gain, depth control, mode change, zoom and pan box control, forward and review of clips. This interface device does not necessarily need to include a keyboard. Thus, this user interface device may be designed to have only a limited set of controls, with the remaining controls including the keyboard accessible via the display screen of the review and imaging system. In this case, the user interface device may comprise a mouse such that a reviewer may use the point and click method to access functions not provided on the user interface device.

Figure 13:
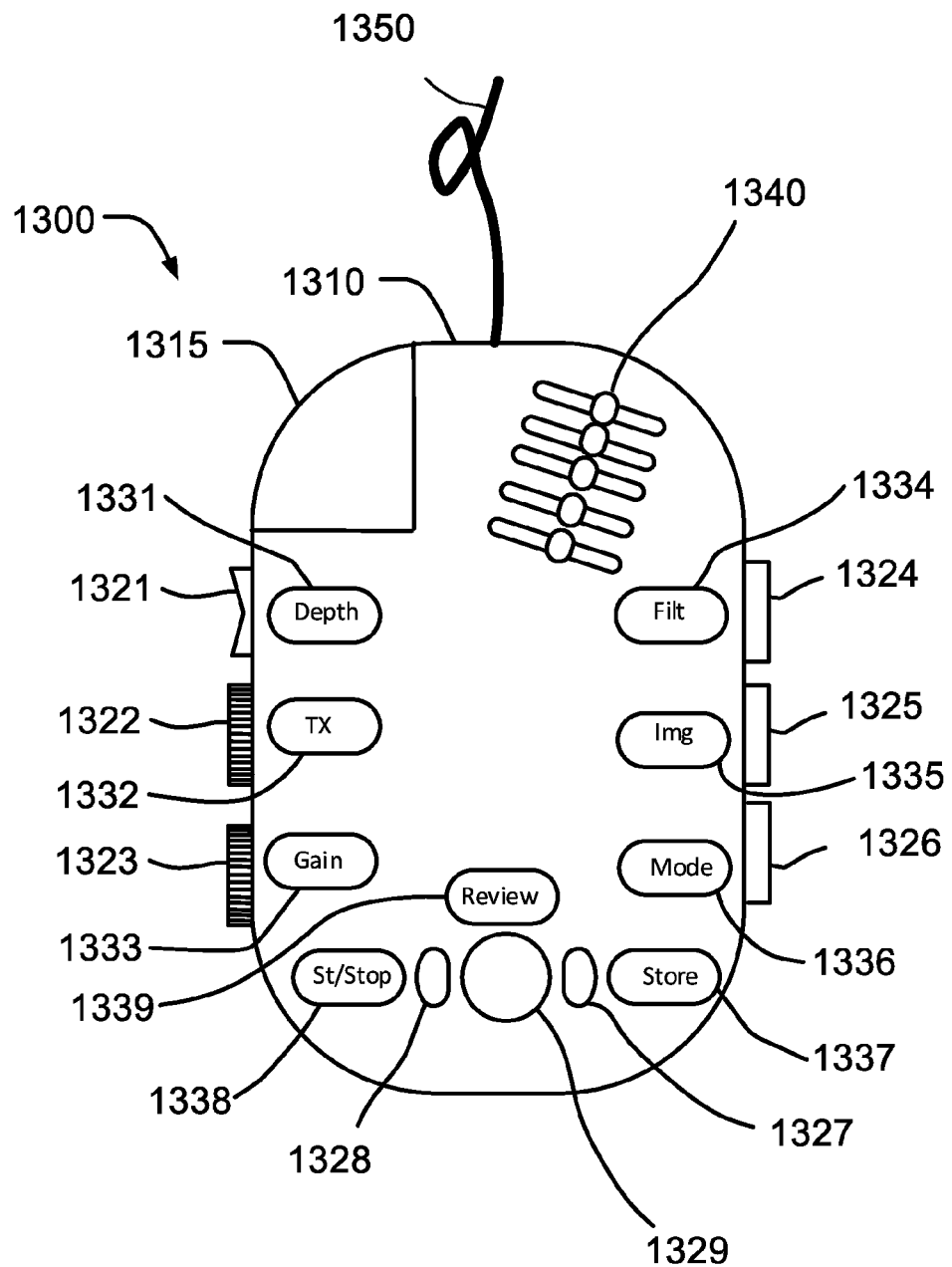
FIG. 13 is a schematic illustration of a user interface device that can be used to operate a review and imaging system according to an example embodiment of the invention.

FIG. 13 is a schematic illustration of a user interface device 1300 used to operate a review and imaging system according to an example embodiment of the invention. User interface device 1300 may have a size and form factor so that it can be comfortably handled by one hand. In some embodiments, the shape of user interface device 1300 may be generally similar to a computer input device such as a mouse.

User interface device 1300 may comprise several types of control inputs arranged around body 1310 of the device. In addition, some or all control inputs may be associated with a display device such that the reviewer may understand the functionality of the control inputs. These display devices may include but may not be limited to miniature liquid crystal displays or backlit cutouts of the surface of user interface device 1300. If cutouts are used, then body 1310 of user interface device 1300 may comprise a clear plastic covering so that no fluids can enter user interface device 1300 but the lights may be seen.

In the example embodiment shown in FIG. 13, each control input is associated with a display device. For example, rocker input 1321 is associated with display device 1331. Similarly, inputs 1322 and 1323 are associated with display devices 1332 and 1333. Side push button inputs 1324, 1325 and 1326 are associated with display devices 1334, 1335 and 1336, top push button inputs 1327 and 1328 are associated with display devices 1337 and 1338, and trackball 1329 is associated with display device 1339.

User interface device 1300 may also comprise slider inputs 1340. In some embodiments, slider inputs 1340 may control the time gain compensation curve or the backend gain over certain depth ranges. In some embodiments, slider inputs 1340 may be arranged at an angle as shown in FIG. 13 so that they are located between the first and second fingers of the reviewer as the reviewer holds device 1400 with his or her palm. User interface device 1300 may also comprise inputs that are traditionally found on a mouse such as clicker input 1315. With clicker input 1315, user interface device 1300 can be used as a traditional point and click device. Using user interface device 1300, a reviewer can control multiple functions of a connected review and imaging system. For example, rocker input 1321 may be actuated to control image depth and thumbwheel input 1322 may be scrolled to control the overall gain.

It is to be understood that while one configuration of the user interface device is illustrated, other configurations with more or fewer inputs and/or actuators, with other types of actuators or with other mappings of the actuators to functions, is possible. In addition, while user interface device 1300 comprises wire 1350 (as seen in FIG. 13), user interface device may also or alternatively comprise a wireless connection.

In another concept, information about the user-interface controls that are implemented on a specific ultrasound machine may be stored and transferred to a review and imaging system. For example, using the DICOM private data facility, information such as but not limited to the location of knobs and other actuators, the function each input and/or actuator activates, the number of settings accessible via each actuator, can be stored and transferred. When this information is transferred to the review and imaging system, it can be mapped to specific controls on the available user interface devices (interfaced to the review and imaging system) or mapped to a radio buttons or other such selection mechanism on the display screen of the review and imaging system.

When extended ultrasound data for a range of different parameter settings is available at a review and imaging system the user interface of the review and imaging system may optionally display or highlight the parameter settings corresponding to data available at the review and imaging system.

Review and Imaging System: Storage of Settings

The review and imaging system provides advantageous ways for a reviewer and/or other personnel to interact with the data stored in the review and imaging system. In one concept, the review and imaging system settings chosen or preferred by a reviewer may be stored within the review and imaging system. These settings may include information such as but not limited to choices of filters and their coefficients, post-processing maps, speckle reduction settings, image enhancement settings, etc. Since images from systems manufactured by different manufacturers may be reviewed at the same review and imaging system, the review and imaging system may be configured to store multiple sets of system settings for multiple ultrasound machines. In other words, a reviewer can store different review and imaging system settings for one or multiple ultrasound machines.

Figure 14:
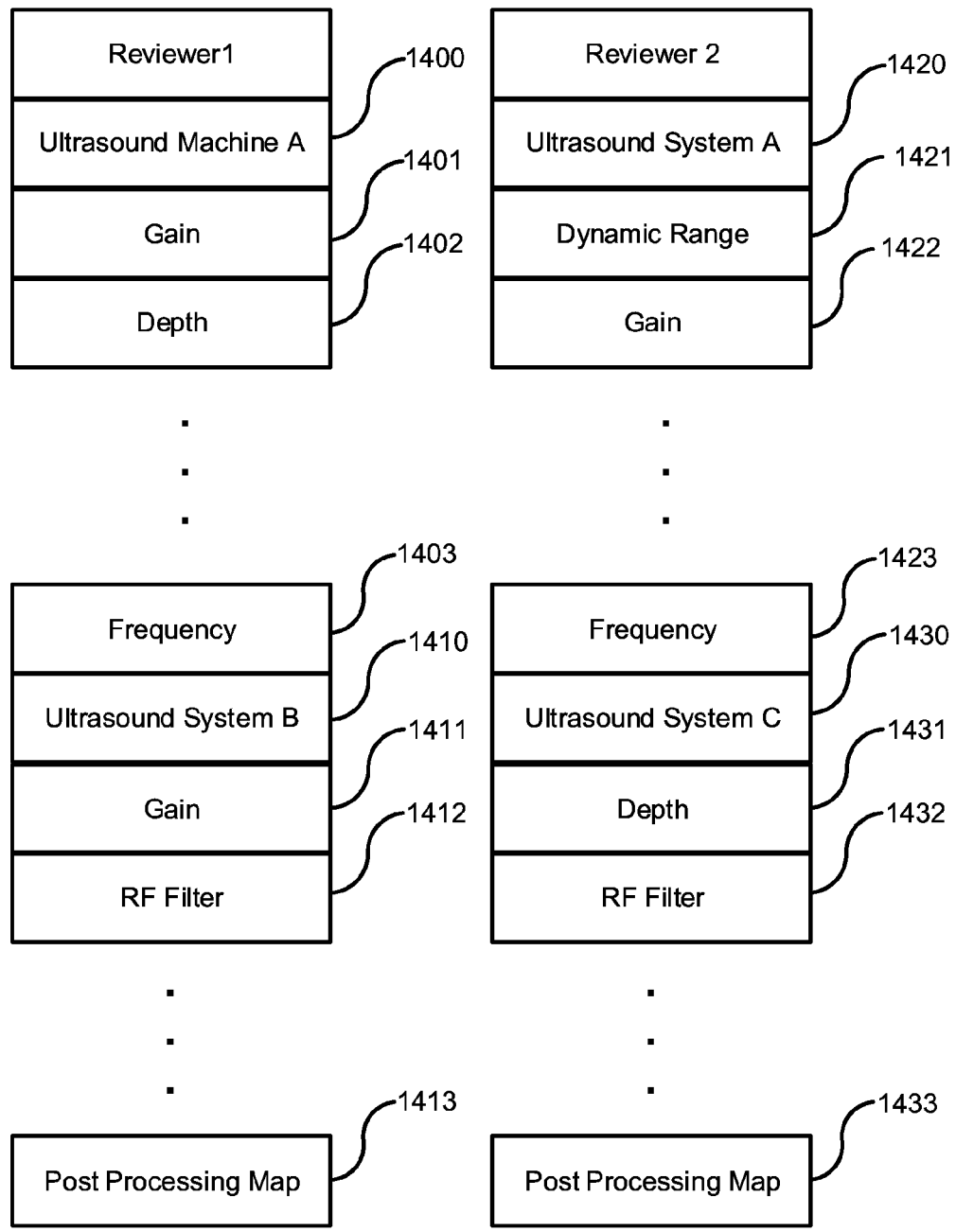
FIG. 14 is a schematic illustration of a memory organization that may be utilized to store a reviewer's preferences for settings and/or values of parameters in the review and imaging system.

FIG. 14 is a schematic illustration of an example memory organization that may be utilized to store a reviewer's preferences for settings and/or values of parameters in a review and imaging system. The reviewer's preferences may be stored in the memory of a review and imaging system (e.g. local storage memory module 830 in FIG. 8).

In the example illustrated in FIG. 14, two reviewers store their preferences and settings in the same review and imaging system. "Reviewer 1" mainly reviews images from ultrasound machine A and ultrasound machine B, while "Reviewer 2" mainly reviews images from ultrasound machine A and ultrasound machine C. Thus, Reviewer 1 may store preferences for parameters including not but limited to gain, imaging depth, and frequency in memory locations 1401, 1402, and 1403 for ultrasound machine A, and preferences for parameters including but not limited to gain, RF filter, and post-processing map in memory locations 1411, 1412, and 1413 for ultrasound machine B. Similarly, Reviewer 2 may store preferences for parameters including not but limited to dynamic range, gain, and frequency in memory locations 1421, 1422, and 1423 for ultrasound machine A, and preferences for parameters including but not limited to depth, RF filter, and post-processing map in memory locations 1431, 1432, and 1433 for ultrasound machine C.

Although FIG. 14 shows one non-limiting example configuration of how preferences and review and imaging system settings may be stored, other configurations are possible. For example, the preferences may be stored according to the transducer used instead of according to ultrasound machine. Thus memory locations 1400, 1410, 1420 and 1430 may be extended include information on the transducer used instead of or in additional to information on the ultrasound machine used.

Actual settings used on the ultrasound machine when the image data was being acquired may also be transferred to and stored on a review and imaging system. The settings can be stored on the review and imaging system using a memory organization similar to the one shown in FIG. 14. The review and imaging system may be configured to automatically display an image based on the closest settings available. For example, if Reviewer 1 prefers an imaging depth of 70 mm for data captured from ultrasound machine A, but the data for this specific imaging depth does not exist on the review and imaging system, the review and imaging system may choose to display available data that is closest to the preference. If data for an imaging depth of 75 mm existed, this data could be presented to the reviewer. Rules may be established within the review and imaging system to accommodate these cases.

Reviewer Interaction with the Review and Imaging System

Figure 15A:
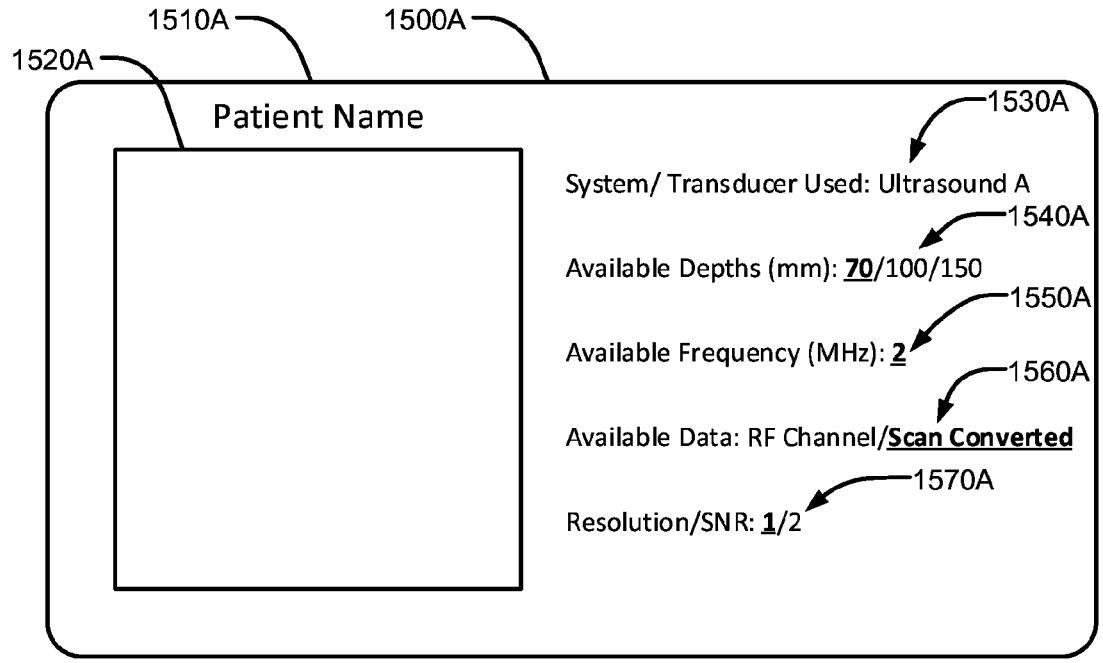
FIGS. 15A and 15B are example illustrations of screen layouts produced by a review and imaging system.
Figure 15B:
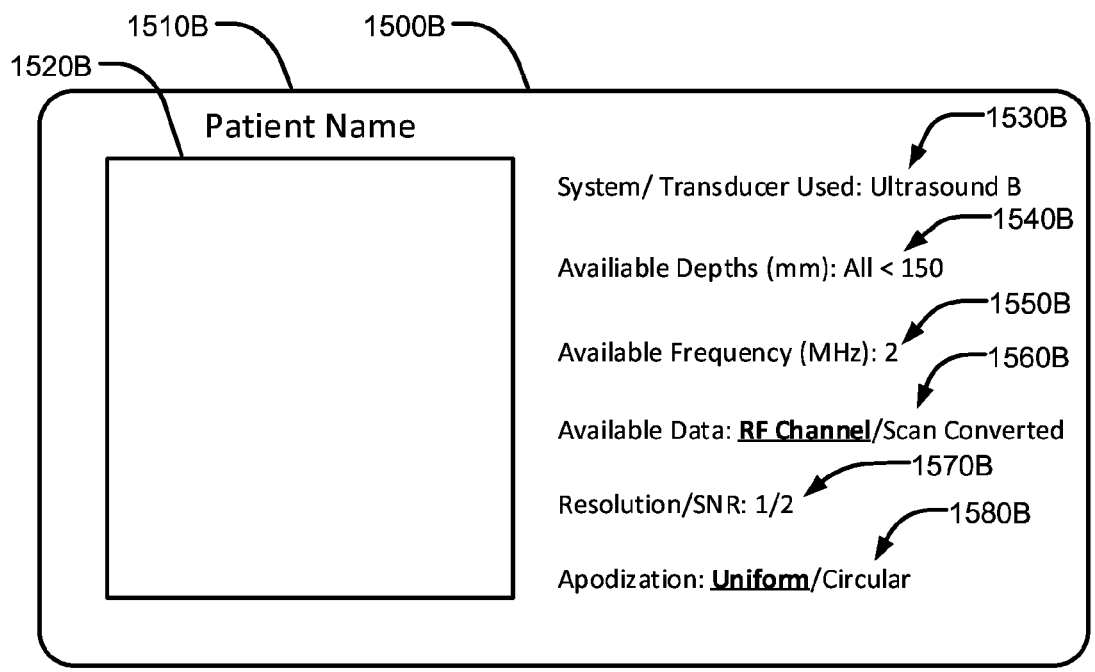

FIGS. 15A and 15B are example illustrations of screen layouts 1500 produced by a review and imaging system. Screen layouts 1500 may be provided on the display of the review and imaging system (e.g. display 860 in FIG. 8). In some embodiments the screen layouts indicate availability of choices for settings for image processing parameters. The available choices may depend, for example, on what additional data is available and/or on what additional data the reviewer has selected to use. FIGS. 15A and 15B respectively correspond to the additional data specified by FIGS. 17A and 17B.

Screen layout 1500 comprises patient name field 1510, ultrasound image display area 1520, system and/or transducer information field 1530, and parameter fields 1540, 1550, 1560 and 1570. In FIG. 15A, parameter field 1540A is labeled "Available Depths (mm)" and shows that imaging depths of 70, 100 or 150 mm are available for the ultrasound image displayed in image display area 1520.

As shown in FIG. 15A at parameter field 1540A, the settings for the depth parameter are displayed as 70/100/150. A reviewer may cycle through these depths as desired using a user interface control (e.g. generalized ultrasound keyboard 1220 in FIG. 12, or user interface device 1300 in FIG. 13. An indication may be included on the screen layout 1500 to indicate the choice. For example, the available depth of 70 mm is bolded and/or underlined (as seen in FIG. 15A) to indicate that this depth has been selected.

In FIG. 15A, there are multiple settings available for parameter fields 1540A, 1560A and 1570A, but only one available setting for each of parameter fields 1530A and 1550A. Parameter field 1350 is labeled "Available freq. (MHz)", and the only frequency available is 2 MHz, while parameter field 1560A is labeled "Available Data", and the choices available are RF channel-by-channel data and Scan converted data. If multiple options are available for a particular parameter field, the reviewer may have the option of cycling through these available choices.

In FIG. 15B, a reviewer has decided to review RF channel data (as indicated by parameter field 1560B). In this situation, additional parameters and/or additional information may be displayed. For example, at parameter field 1540B, a new phrase "All<150" appears. This indicates that for the channel-by-channel RF data associated with the particular exam being reviewed, the reviewer has a choice of multiple depths as long as the chosen depth is less than 150 mm. This choice was unavailable in the example of FIG. 15A because the reviewer had selected scan converted data to review in that case. Screen layout 1500B also comprises additional parameter field 1580B. Here, the parameter is "Apodization" and the reviewer has a choice of uniform or circular types of apodization. This choice is available because RF channel data was selected for review.

As shown in FIG. 15B, the number of parameter fields and the values for the parameters for which a reviewer may select may depend on the data type. The rules that govern the choice of parameters and their possible settings can be programmed within the review and imaging system and may reside as programs within either a processing module or a graphics module (e.g. processing unit 810 or GPU 820 in FIG. 8). These programs may examine the input data and determine the choices available for the reviewer. For example, if the user captured channel-by-channel RF data with circular apodization applied, then no choice for apodization would be provided at parameter field 1580B.

Data Transfer Between Ultrasound Machine and Review and Imaging System

To enable many of the advantages of a review and imaging system, an ultrasound machine provides data to a review and imaging system. The data may be provided directly or via an intermediate device such as a server or an archival system. The data transferred to the review and imaging system includes at least one or more of: ultrasound data (of one or more types that exist within the ultrasound machine), parameters and settings, algorithms, and ultrasound machine hardware and software configuration.

One mechanism to enable the transfer and interpretation of such information is to use the private mode within the DICOM standard. The use of private mode data typically involves a private mode encoder and a private mode decoder. A private mode encoder may be provided at the ultrasound machine. A corresponding private mode decoder may exist within the review and imaging system.

Since the review and imaging system may accept data from one or multiple different models and/or brands of ultrasound machines, one or multiple private mode decoders may be provided at the review and imaging system. The private mode decoders may, for example, comprise private mode decoding hardware and/or private mode decoding software that executes on a processor at the review and imaging system. The review and imaging system may be instructed to choose the appropriate private data decoding program in multiple ways including but not limited to by using the ultrasound machine specific information transferred as part of information transferred when DICOM is used (i.e. in non-private mode) or by configuring the various ultrasound machines to encode the system configuration information in a standard way.

Figure 16:
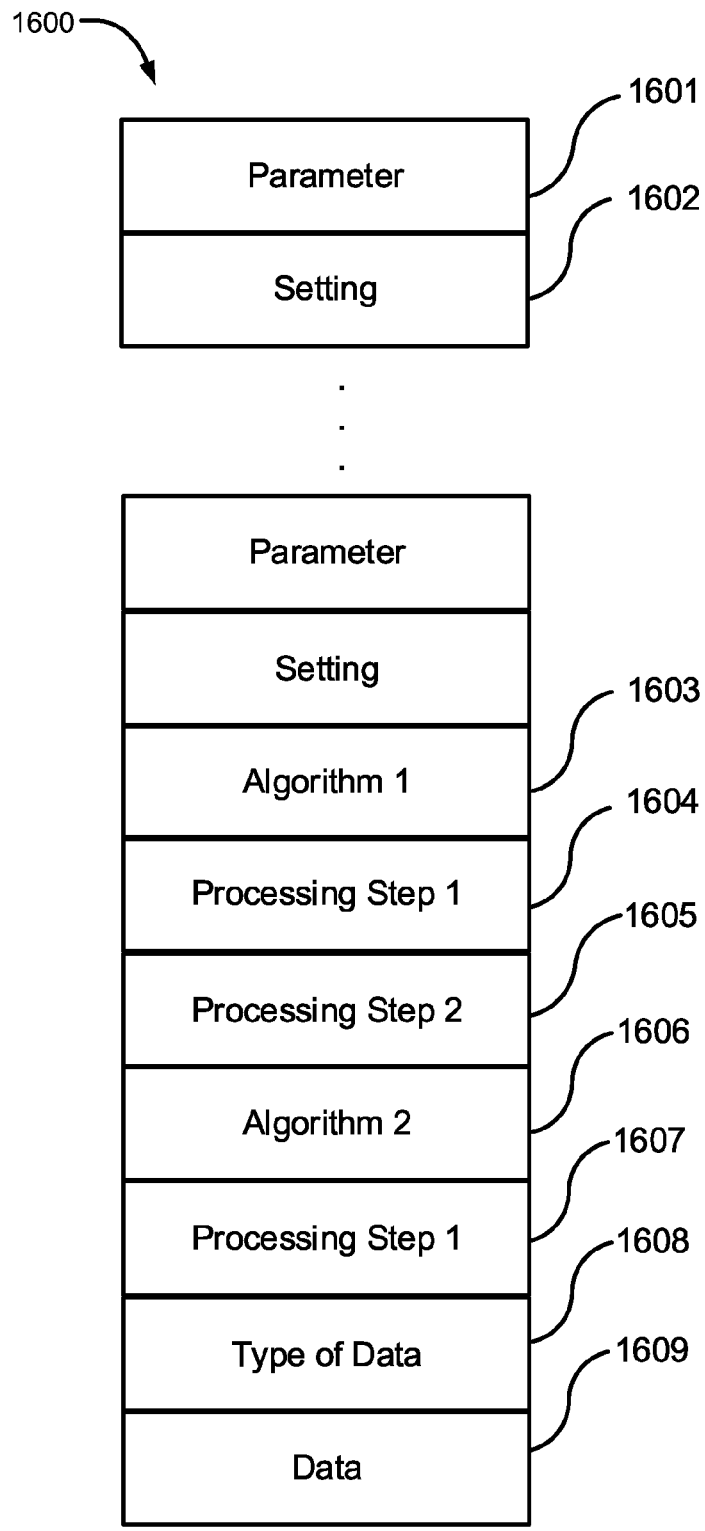
FIG. 16 is a schematic illustration of a memory organization that may be utilized to store data, parameters, algorithms and other information within the memory of an ultrasound machine.

FIG. 16 is a schematic illustration of a memory organization 1600 that may be utilized to store data, parameters, algorithms and other information within the memory of an ultrasound machine. While other configurations are possible, the general construct shown in FIG. 16 is that metadata about the information is stored first, followed by the data itself. The metadata may contain various types of information including but not limited to instructions of the sequence of the application of the algorithms. Once the entire information is collected, this information may be encoded by a private mode encoder within the ultrasound machine. Thus, as indicated by memory locations 1601 and 1602, the relevant parameters and settings associated with the data being captured may be stored along with the data.

Similarly, algorithms may also be specified as part of memory organization 1600. Two example algorithms are illustrated in 1603 and 1606. Algorithm 1 may comprise two processing steps as indicated by memory locations 1604 and 1605, while algorithm 2 may comprise a single processing step stored at memory location 1607. Finally, memory location 1608 indicates the type of data being stored and memory location 1609 stores the data. When all the information in memory organization 1600 is encoded and subsequently decoded within the review and imaging system, the decoded information may be organized in a similar manner to that shown in FIG. 16.

If RF data is being stored within the ultrasound machine, information that is encoded may include but may not be limited to sampling rate, transmit frequency and receive apodization. Information that is encoded may also include general information such as but not limited to number of transmit channels, number of receive channels, transducer information, actual frame rate achieved by the system when the data was processed through the ultrasound machine, etc. Further, the information that is encoded may also include the various algorithms and processing steps that the ultrasound machine would have applied downstream of where the data was captured. Inclusion of such algorithms is one way to allow the review and imaging system to accurately emulate the results that could be achieved at the ultrasound machine.

The memory configuration and types of metadata stored may be different depending on the type of data being stored. For example, if detected line-by-line data is being captured and stored by the ultrasound machine, the sampling frequency does not need to be stored.

To ensure that the appropriate data is collected and encoded, a process may be implemented on the ultrasound machine to automatically collect extra information when a user indicates that he or she wants to store data. The process may optionally ask the user to indicate the type of data that is desired and based on this, may determine other information that may be needed to interpret and process the data. For example, the process may collect, store and encode the general information about the system regardless of data that is being captured and stored.

At the review and imaging system, this information is decoded by a private mode decoder (e.g. image decoder 821 in FIG. 8). The private mode decoder may decode and organize the information in any suitable manner. For example, the decoded information may be stored in a data structure or structures similar to the organization within the ultrasound machine when it was encoded. A process controller (e.g. processing unit 810 in FIG. 8) may examine this data and parse out various pieces of information to various image processing modules. The process controller may also obtain information about the sequence of operations to be performed on the image data based on information that is encoded and decoded. Using this information, the process controller may schedule various tasks within the review and imaging system.

Example Sequence of Operations

Figure 20:
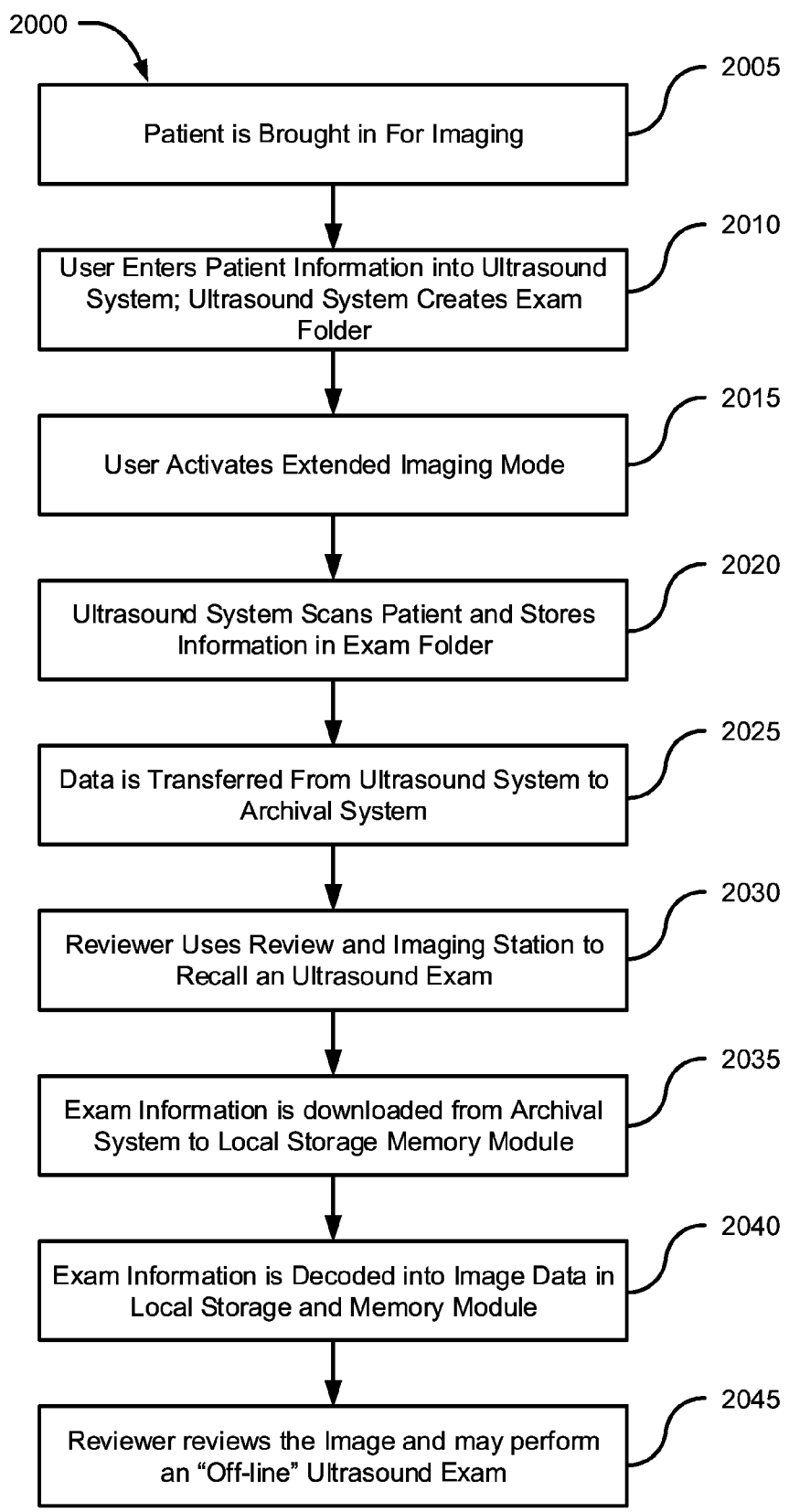
FIG. 20 is a flowchart illustrating a sequence of operations performed by the user, the ultrasound machine, the reviewer and the review and imaging system according to an example embodiment of the invention.

FIG. 20 illustrates a sequence of operations 2000 that may be performed by the user, the ultrasound machine, the reviewer and the review and imaging system. In box 2005, the patient is brought in for imaging. In box 2010, the user enters patient information into the ultrasound machine. This action results in the opening of an exam folder that is used to store the images and other information about the patient. Following this, in box 2015, the user scans or images the patient and activates the extended imaging mode. As described earlier, when this mode is activated, data types that exist within the ultrasound machine but are typically not captured may now be captured and stored. In box 2020, the ultrasound machine stores the ultrasound data and other information within the exam folder. In box 2025, after the patient examination is complete, exam data is typically encoded or formatted for example using the DICOM format and transferred from the ultrasound machine to the archival system.

In box 2030, the reviewer selects an exam to review from a list of exams. In box 2035, the exam data is downloaded from the archival system to the local storage memory module. In box 2040 exam data is decoded (from the DICOM format if that format is used) into image data in the local storage memory module. Since various types of data types may be captured and stored, various operations can be performed by the reviewer. As is illustrated in box 2045, due to being able to perform various operations, the reviewer can essentially perform an "off-line ultrasound exam". In other words, as long as the appropriate data type has been captured, stored and transferred, the reviewer can manipulate and change the image on the review and imaging system, similar to what can be done on an actual ultrasound machine. The benefit of this feature is that this can be done while the patient is no longer physically present.

For example, if a reviewer determines that there is not enough penetration in an image to see a deep lesion, the patient would conventionally have to be recalled for a repeat ultrasound exam utilizing a lower frequency. However, with the extended imaging mode, it may be possible to acquire and store ultrasound data acquired using a lower frequency (even if the user of the ultrasound machine does not choose to use that lower frequency) and have that ultrasound data readily available so that the diagnosis can be performed without having to recall the patient.

Machine-Driven Analysis

In all the examples above, the reviewer was assumed to be a human. However, the review and imaging system may be utilized in a machine-driven analysis or a combination of a human-machine driven analysis. Machine-driven analysis or human-machine driven analysis may be beneficial in a variety of ways including but not limited to reducing the workload strain of the reviewer or increasing the confidence that the pertinent information from the images from a particular patient has been examined.

In some embodiments, a user interface (e.g. user interface 840) is provided for a reviewer to invoke a machine-driven analysis or a combination human-machine driven analysis. In one example of such an interface, the review and imaging system may have a control (for example a radio button on the display screen) which if selected, instructs the review and imaging system to perform a machine driven analysis of the images the reviewer is currently reviewing. The user interface may also allow the reviewer to select the type of machine driven analysis that is to be performed. Various types of machine driven analysis may be provided. Some types of machine-driven analysis may be pre-programmed and accessible to the review and imaging system. The reviewer has the option of selecting one or several of these preprogrammed analysis packages.

An example preprogrammed machine driven analysis may perform the following steps:

a. For the image on the screen, obtain the corresponding RF data from memory.
b. Prompt the reviewer to draw a region of interest on the screen.
c. Prompt the reviewer to identify the main anatomy within the region of interest such as kidney or liver or mitral valve etc. The reviewer enters the name of the anatomy into the review and imaging system.
d. Check if "normal" (the definition of "normal" is provided below) information is present within the review and imaging system for the specified anatomy. If information is not present, alert the reviewer who can the make other choices.
e. Divide the region of interest into smaller regions of interest and perform feature extraction from the RF data within the boundaries of the smaller regions of interest for all such smaller regions. (For reference, features here refers to characteristics of the RF data such as but not limited to mean, standard deviation, or any higher order statistical parameters)
f. Compare the value of the features for each of the smaller regions to a predetermined set of values of the same features where the predetermined set is considered to be normal for the anatomy being examined. The predetermined set of values may already be preprogrammed within the review and imaging system.
g. If the values of the features are outside a threshold of the "normal" values, highlight the specific smaller region and display the highlight on the screen.

The review and imaging system may also allow the reviewer to customize the analysis. A user interface may be provided where the reviewer can specify the type of analysis that is desired. The specification may be done in a language that can be interpreted by the review and imaging system. To simplify this process, the user interface may provide drop down menus to allow the reviewer to select from a number of different options. As an example, through drop down menus, the reviewer may be given a choice of the type of data to analyze (e.g. the type of data may include, without limitation, RF data, line-by-line detected data, scan converted data etc.). The interface may also provide an input that the reviewer may use to select a type of analysis algorithm to be used. Examples may include algorithms that extract first order and/or higher order statistics.

Thus, the reviewer may control the review and imaging system (e.g. through a series of drop down menus) to customize the analysis. Once the reviewer customizes the type of analysis, the CPU or other computing modules within the review and imaging system (e.g. processing unit 810) may parse or interpret these instructions, generate low level instructions if necessary, and execute the commands within the appropriate module.

In another concept, the review and imaging system is configured for performing machine learning. A machine learning algorithm may be included as part of the analyzer module (e.g. image analyzer 824). The review and imaging system provides an interface for the reviewer to interact with the machine learning module. For reference, in a machine learning tool, a training set is provided to the system where the training set is annotated. For this example, the user interface of the review and imaging system may allow the reviewer to select one or multiple images, pick a region or regions within each image, and annotate these regions with names of the anatomy and descriptions such as but not limited to "healthy" or "lesion".

The annotated regions may be submitted to train the machine learning module. Over time, the review and imaging system may build a library of annotated information for different anatomies. This forms the training set. The machine learning module may use this information and generate an internal list of features that it uses to classify if a particular anatomy is healthy or otherwise. Given sufficient training data, the machine learning algorithm may learn to determine the type of issue associated with an unhealthy anatomy. After the initial training is complete (determined by if a test image presented to the machine learning algorithm is analyzed in the same way as is a reviewer had analyzed the image), the reviewer may select this type of machine learning through the user interface to aid in the review process. Thus, this type of machine learning provides an opportunity for the review and imaging system to "learn" how a reviewer analyzes images and produce results of analysis as if the reviewer had performed the analysis.

In another aspect, the review and imaging system provides a user interface that allows the reviewer to accept the results of the machine driven analysis or reject it. If the reviewer accepts the results (for example by clicking on a radio button or operating another control), the results may be sent to a further process that summarizes the results. If the results are not accepted, the user interface allows the reviewer to enter the new results. Apart from summarizing the results, the review and imaging system may use these results to further train the machine learning algorithm.

Data Management

Application of some or all of the various concepts and aspects described herein may result in capture and subsequent transfer and processing of large amounts of data. The concepts below provide some ways to manage this data. In one concept, a system as described herein may incorporate rules that determine how much data of one or more data types is transferred to a review and imaging system and/or when such data is transferred to the review and imaging system. Such rules may be applied at an ultrasound machine and/or an archival system, for example. In some implementations the user may configure a rule using an interface of the ultrasound machine. In other implementations rules may be incorporated into one or more predefined schemas for data acquisition. Rules may specify things such as: how many frames of data to acquire (e.g. every frame, every other frame, every $N^{th}$ frame where N is an integer), what are triggers for acquiring data of a particular type, etc.

In an example embodiment, tables which may be similar to those illustrated in FIGS. 17A, 17B, and 17C are extended to include settings that specify how much data to acquire. These settings may be set or selected by a user. For example, FIG. 21 shows a case where FIG. 17C is extended to include a column with the heading "Rule for amount of data to be captured". The entries in this column may specify rules in a number of ways which may include, without limitation, using a formatted language that a controller (e.g. controller 510) may interpret. A user may operate a user interface of an ultrasound machine to load or specify appropriate rules.

In the example shown in FIG. 21, the user has entered a rule that specifies that when RF data is collected, only one frame of RF data is to be captured every 0.5 s (or other time period). Examples of other rules could include without limitation rules which cause the ultrasound machine to:

capture one or another specified number of frames of RF data every time a frozen scan converted image is captured;

capture a specified number of frames of scan-converted detected data within specified time intervals (e.g. 2 frames every 2 s); and/or capture all of a specific type of data during a specified time period.

For example, the phrase "RF: ALL" in the last column would mean that every frame of RF data is to be captured during the 5 s interval.

Interpretation of Terms

Unless the context clearly requires otherwise, throughout the description and the "comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Implementations of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for an ultrasound review station or an ultrasound review and imaging system or an ultrasound imaging machine or an ultrasound archival system may implement methods as described herein by executing software instructions in a program memory accessible to the processors and/or by processing data according to logic configured in a logic circuit or configurable device such as an FPGA.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Some aspects of the invention may be provided in the form of a program product. The program product may comprise any non-transitory medium which carries a set of computer-readable instructions which, when executed by a data processor, cause the data processor to execute a method of the invention (e.g. a method performed by an ultrasound machine or a method performed by a review and imaging system). Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some implementations, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary implementations of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described implementations that would be apparent to the skilled addressee, including variations obtained by: replacing features, elements and/or acts with equivalent features, elements and/or acts; mixing and matching of features, elements and/or acts from different implementations; combining features, elements and/or acts from implementations as described herein with features, elements and/or acts of other technology; and/or omitting combining features, elements and/or acts from described implementations.

It is therefore intended that claims hereafter introduced are interpreted to include all such modifications, permutations, additions, omissions, and sub-combinations as may reasonably be inferred. The scope of the claims should not be limited by the preferred implementations set forth in the examples, but should be given the broadest interpretation consistent with the description as a whole.

What is claimed is:

1. An ultrasound imaging system comprising:
at least one ultrasound imaging machine operable by a user to acquire first image data that can be processed to display a first ultrasound image, the first image data acquired according to user settings for one or more parameters that affect quality of the first image data;
at least one review and imaging system in data communication with the ultrasound imaging machine, the review and imaging system operable to process data originating from the ultrasound imaging machine and to display a resulting image on a display of the review and imaging system;
the ultrasound imaging machine comprising an ultrasound transmitter, an ultrasound receiver connected to receive ultrasound echo signals from an ultrasound transducer, an image processing chain configured to process the echo signals to yield image data, a display operative to display the first ultrasound image represented by the first image data and a user interface operative to receive user inputs for configuring the user settings and controlling the ultrasound machine to acquire the first image data using the user settings for the one or more parameters that affect quality of the first image data;
wherein the ultrasound machine is configured to:
automatically alter the user settings to obtain altered settings different from the user settings, transmit ultrasound energy and receive corresponding echo signals, and process the echo signals to obtain second image data that can be processed to display at least one second ultrasound image, wherein at least one of transmitting the ultrasound energy and receiving the ultrasound energy to obtain the second image data is based on the altered settings; and make the first image data and additional data including the second image data, available to the review and imaging system such that a reviewer using the review and imaging system can cause the review and imaging system to display the first ultrasound image or any of the at least one second ultrasound images on the display of the review and imaging system.

2. The system according to claim 1 wherein the additional data comprises one or more of channel-by-channel RF data, summed line-by-line RF data, detected line-by-line data and pre-scan converted image data.

3. The system according to claim 1 wherein the review and imaging system comprises a user interface that provides controls operable to adjust select settings that affect quality of the resulting image.

4. The system according to claim 3 wherein the review and imaging system is configured to process the additional data to determine available settings wherein the available settings comprise one or more altered settings for each of one or more parameters that correspond to the additional data and are therefore available for selection to alter the quality of an image displayed by the review and imaging system and to display the available settings.

5. The system according to claim 3 wherein the user interface of the review and imaging system comprises a control operable to select an imaging depth different from an imaging depth specified in the user settings.

6. The system according to claim 3 wherein the user interface of the review and imaging system comprises a control operable to select a transmit focus different from a transmit focus specified in the user settings.

7. The system according to claim 3 wherein the user interface of the review and imaging system comprises a control operable to adjust a gain.

8. The system according to claim 7 wherein the control is operable to adjust gain on a line-by-line basis.

9. The system according to claim 3 wherein the user interface of the review and imaging system comprises a control operable to select a transmit frequency.

10. The system according to claim 1 wherein the user settings include a transmit frequency and the altered settings include an altered transmit frequency different from the transmit frequency wherein the ultrasound machine is configured to: automatically alter a transmit frequency specified in the user settings to the altered transmit frequency; operate the transmitter to transmit ultrasound energy at the altered transmit frequency and operate the receiver to receive corresponding echo signals; and include in the additional data the corresponding echo signals or data obtained by processing the corresponding echo signals.

11. The system according to claim 10 wherein the user interface of the review and imaging system comprises a control operable to select the transmit frequency.

12. The system according to claim 1 wherein the ultrasound machine is configured to, in sequence, obtain a plurality of sets of the additional data, each of the sets of the additional data comprising the second image data obtained using different altered settings and to make the plurality of sets of the additional data available to the review and imaging system.

13. The system according to claim 1 wherein the review and imaging system provides a multi-stage image processing chain, the additional data includes data of at least one of plural types of data, the plural types present at corresponding stages of the image processing chain of the ultrasound machine, and the review and imaging system is configured to input the additional data into a stage of the multi-stage image processing chain based on the type of the data.

14. The system according to claim 1 wherein the additional data comprises data specifying a control layout for the ultrasound machine and the review and imaging system is configured to assign functions to the controls of the user interface of the review and imaging system based on the control layout for the ultrasound machine.

15. The system according to claim 1 wherein the additional data comprises data specifying one or more image processing algorithms included in the image processing chain of the ultrasound machine and the review and imaging system is configured to apply the one or more image processing algorithms in processing the additional data.

16. The ultrasound imaging system according to claim 1 wherein the one or more parameters that affect quality of the image data comprise at least one ultrasound parameter wherein settings of the ultrasound parameter alter one or more characteristics of ultrasound emitted by the ultrasound transmitter;

wherein the ultrasound imaging machine is configured to:
a) set the ultrasound parameter to a first setting based on inputs received by way of the user interface, acquire a first ultrasound image by transmitting ultrasound according to the first setting of the ultrasound parameter, receiving echo signals corresponding to the first setting of the ultrasound parameter and processing the signals to yield the first ultrasound image; and,
b) automatically change the ultrasound parameter to a second setting different from the first setting and automatically acquire ultrasound data for a second image by transmitting ultrasound according to the second setting of the ultrasound parameter and receiving echo signals corresponding to the second setting of the ultrasound parameter;

wherein the additional data comprises the ultrasound data for the second image or data obtained by processing the ultrasound data for the second image.

17. The ultrasound imaging system according to claim 16 wherein the at least one ultrasound parameter comprises at least one of: an imaging depth; a transmit focus; a transmit frequency; and an apodization function.

18. The ultrasound imaging system according to claim 16 wherein the ultrasound data for the second image is radio-frequency (RF) data or pre-scan converted detected data.

19. The ultrasound imaging system according to claim 16 wherein the ultrasound machine is configured to determine the second setting for the ultrasound parameter based on the first setting for the ultrasound parameter.

* * * * *